(12) United States Patent
Svrluga et al.

(10) Patent No.: US 10,342,900 B2
(45) Date of Patent: *Jul. 9, 2019

(54) DRUG DELIVERY SYSTEM AND METHOD OF MANUFACTURING THEREOF

(75) Inventors: Richard C. Svrluga, Cambridge, MA (US); Sean R. Kirkpatrick, Littleton, MA (US); Stephen M. Blinn, Amherst, NH (US)

(73) Assignee: EXOGENESIS, Billerica, MA (US)

( * ) Notice: Subject to any disclaimer, the term of this patent is extended or adjusted under 35 U.S.C. 154(b) by 103 days.

This patent is subject to a terminal disclaimer.

(21) Appl. No.: 13/591,837

(22) Filed: Aug. 22, 2012

(65) Prior Publication Data

US 2013/0218264 A1 Aug. 22, 2013

Related U.S. Application Data

(60) Provisional application No. 61/526,186, filed on Aug. 22, 2011.

(51) Int. Cl.
*A61L 31/16* (2006.01)
*A61L 27/54* (2006.01)
*A61K 31/436* (2006.01)

(52) U.S. Cl.
CPC ............ *A61L 31/16* (2013.01); *A61K 31/436* (2013.01); *A61L 27/54* (2013.01); *A61L 2300/602* (2013.01); *A61L 2300/606* (2013.01); *A61L 2300/61* (2013.01); *A61L 2400/18* (2013.01); *A61L 2420/02* (2013.01)

(58) Field of Classification Search
USPC ................ 427/2.24, 2.25, 523, 534; 250/251
See application file for complete search history.

(56) References Cited

U.S. PATENT DOCUMENTS

| 3,679,897 A | 7/1972 | Hansen |
| 4,935,623 A * | 6/1990 | Knauer ............... H05H 3/02 118/715 |
| 6,486,478 B1 | 11/2002 | Libby |
| 6,491,800 B2 | 12/2002 | Kirkpatrick et al. |
| 6,676,989 B2 | 1/2004 | Kirkpatrick et al. |
| 7,105,199 B2 * | 9/2006 | Blinn et al. ............ 427/2.24 |

(Continued)

FOREIGN PATENT DOCUMENTS

| CA | 2638020 | 8/2007 |
| JP | 1985-124931 | 4/1985 |

(Continued)

OTHER PUBLICATIONS

Wegner, et al. (2006), "Gas-phase synthesis of nanostructured particulate films", KONA Powder and Particle, 24, 54-69.

(Continued)

*Primary Examiner* — Dah-Wei D. Yuan
*Assistant Examiner* — Andrew J Bowman
(74) *Attorney, Agent, or Firm* — Burns & Levinson LLP; David W. Gomes

(57) ABSTRACT

A method of modifying the surface of a medical device to release a drug in a controlled way by providing a barrier layer on the surface of one or more drug coatings. The barrier layer consists of modified drug material converted to a barrier layer by irradiation by an accelerated neutral beam derived from an accelerated gas cluster ion beam. Also medical devices formed thereby.

12 Claims, 25 Drawing Sheets

(56) References Cited

U.S. PATENT DOCUMENTS

| | | | |
|---|---|---|---|
| 7,247,845 | B1 | 7/2007 | Gebhardt et al. |
| 8,629,393 | B1* | 1/2014 | Kirkpatrick ............ H01J 37/05 |
| | | | 250/251 |
| 8,764,952 | B2 | 7/2014 | Sato |
| 9,114,195 | B2* | 8/2015 | Khoury ................... A61L 27/54 |
| 9,799,488 | B2* | 10/2017 | Kirkpatrick ......... H01J 37/3171 |
| 9,808,344 | B2* | 11/2017 | Khoury ..................... A61F 2/28 |
| 2001/0054686 | A1 | 12/2001 | Torti et al. |
| 2003/0021908 | A1 | 1/2003 | Nickel et al. |
| 2003/0026990 | A1 | 2/2003 | Yamada et al. |
| 2006/0043317 | A1 | 3/2006 | Ono et al. |
| 2006/0097185 | A1 | 5/2006 | Mack |
| 2007/0185483 | A1 | 8/2007 | Pohjonen |
| 2008/0169416 | A1 | 1/2008 | Thompson et al. |
| 2009/0140165 | A1 | 6/2009 | Hautala et al. |
| 2009/0321658 | A1 | 12/2009 | Kirkpatrick et al. |
| 2010/0036482 | A1 | 2/2010 | Svrluga et al. |
| 2010/0227522 | A1 | 9/2010 | Khoury et al. |
| 2010/0227523 | A1 | 9/2010 | Khoury et al. |
| 2011/0155897 | A1* | 6/2011 | Harrison ....................... 250/251 |
| 2011/0300599 | A1 | 12/2011 | Khoury et al. |
| 2012/0045615 | A1 | 2/2012 | Kirkpatrick et al. |
| 2014/0236286 | A1 | 8/2014 | Kirkpatrick |

FOREIGN PATENT DOCUMENTS

| | | |
|---|---|---|
| JP | 2001-509638 | 7/2001 |
| RU | 2014110963 | 7/2016 |
| WO | 2012103229 A1 | 8/2012 |

OTHER PUBLICATIONS

International Search Report and Written Opinion dated Dec. 22, 2011 for International Application No. PCT/US11/48754.

International Search Report and Written Opinion dated Nov. 6, 2012 for International Application No. PCT/US12/51868.

International Search Report and Written Opinion dated May 29, 2012 for International Application No. PCT/US12/22567.

International Search Report dated Nov. 6, 2012 and Written Opinion of the International Searching Authority PCT/US12/51868 dated Aug. 22, 2012.

Israel Patent Office action dated Dec. 20, 2016, IL Patent Application 231068.

Oyo Butsuri, 1982, vol. 51, No. 9, pp. 1006-1012 cited in Japan Patent Application No. 2014-088011, Patent Office unit 2927 4U00 reference D3.

Japan Society for the Promotion of Science 132nd Committee, Election and Ion Beam Handbook, Nikkan Kogyo Shimburi, Ltd. Oct. 28, 1998, Third Edition, First Printing, pp. 389-432, cited in Japan Patent Application No. 2014-088011, Patent Office unit 2927 4U00 reference D4.

Office Action of Japan Patent Office for JP national phase cited in Japan Patent Application No. 2014-088011, Patent Office unit 2927 4U00, dispatch date: Jan. 24, 2017 (translation provided).

European Examination Report in corresponding European Application No. 11820497.3, dated Jun. 28, 2017.

Suzuki "Size selection and focusing of neutral carbon clusters" Chemical Physics letters 182(1):12-16 (1991).

Abshagen "Neutral mass-selected lead cluster beams" Atoms, Molecules and Clusters, 19(4):199-201 (1991).

Arnold "Methods for generating neutral, mass-selected cluster beams" Surface Science 156:149-156 (1985).

Office Action in corresponding Canadian Application No. 2,845,762 dated Sep. 8, 2017.

European Search Report in corresponding European Application No. 11820497.3 dated Jun. 23, 2016.

Kirkpatrick, "Gas cluster ion beam applications and equipment" Nuc. Inst. and Meth. in Physics Res. B 206 830-837 (2003).

Gardener et al., "A large area thermal detector for fast neutral particles" J. of Physics E: Scientific Inst. 5: 712-714 (1972).

* cited by examiner

DRUG DELIVERY SYSTEM AND METHOD OF MANUFACTURING THEREOF

CROSS REFERENCE TO RELATED APPLICATIONS

This application claims priority from U.S. Provisional Patent Application No. 61/526,186, filed on Aug. 22, 2011, and incorporated herein by reference in its entirety for all purposes.

FIELD OF THE INVENTION

This invention relates generally to drug delivery systems such as, for example, medical devices implantable in a mammal (e.g., coronary and/or vascular stents, implantable prostheses, etc.), and more specifically to a method and system for applying drugs to the surface of medical devices and/or for controlling the surface characteristics of such drug delivery systems such as, for example, the drug release rate and bio-reactivity, using beam technology, preferably through the use of an accelerated neutral gas cluster beam (GCIB) or an accelerated neutral monomer beam, wherein the accelerated neutral gas cluster beam or accelerated neutral monomer beam is derived from an accelerated gas cluster ion beam. Such technology is applied in a manner that promotes efficacious release of the drugs from the surface over time.

BACKGROUND OF THE INVENTION

Medical devices intended for implant into or for direct contact with the body or bodily tissues of a mammal (including a human), as for example medical prostheses or surgical implants, may be fabricated from a variety of materials including various metals, metal alloys, plastic, polymer, or co-polymer materials, solid resin materials, glassy materials and other materials as may be suitable for the application and appropriately biocompatible. As examples, certain stainless steel alloys, cobalt-chrome alloys, titanium and titanium alloys, biodegradable metals like iron and magnesium, polyethylene and other inert plastics have been used. Such devices include for example, without limitation, vascular stents, artificial joint prostheses (and components thereof), coronary pacemakers, etc. Implantable medical devices are frequently employed to deliver a drug or other biologically active beneficial agent to the tissue or organ in which it is implanted.

A coronary or vascular stent is just one example of an implantable medical device that has been used for localized delivery of a drug or other beneficial agent. Stents may be inserted into a blood vessel, positioned at a desired location and expanded by a balloon or other mechanical expansion device. Unfortunately, the body's response to this procedure often includes thrombosis or blood clotting and the formation of scar tissue or other trauma-induced tissue reactions at the treatment site. Statistics show that restenosis or re-narrowing of the artery by scar tissue after stent implantation occurs in a substantial percent of the treated patients within only six months after these procedures, leading to severe complications in many patients.

Coronary restenotic complications associated with stents are believed to be caused by many factors acting alone or in combination. These complications can be reduced by several types of drugs introduced locally at the site of stent implantation. Because of the substantial financial costs associated with treating the complications of restenosis, such as catheterization, re-stenting, intensive care, etc., a reduction in restenosis rates would save money and reduce patient suffering.

There are many current popular designs of coronary and vascular stents. Although the use of coronary stents is growing, the benefits of their use remain controversial in certain clinical situations or indications due to their potential complications. It is widely held that during the process of expanding the stent, damage occurs to the endothelial lining of the blood vessel triggering a healing response that re-occludes the artery. To help combat that phenomenon, drug-bearing stents have been introduced to the market to reduce the incidence of restenosis or re-occluding of the blood vessel. These drugs are typically applied to the stent surface or mixed with a liquid polymer or co-polymer that is applied to the stent surface and subsequently hardens. When implanted, the drug elutes out of the polymeric mixture in time, releasing the medicine into the surrounding tissue. There remain a number of problems associated with this technology. Because the stent is expanded at the diseased site, the polymeric material has a tendency to crack and sometimes delaminate from the stent surface. These polymeric flakes can travel throughout the cardio-vascular system and cause significant damage. There is evidence to suggest that the polymers themselves cause a toxic reaction in the body. Additionally, because of the thickness of the coating necessary to carry the required amount of medicine, the stents can become somewhat rigid making expansion difficult. Also, because of the volume of polymer required to adequately contain the medicine, the total amount of medicine that can be loaded may be undesirably reduced.

In other prior art stents, the bare wire or metal mesh of the stent itself is coated with one or more drugs through processes such as high pressure loading, spraying, and dipping. However, loading, spraying and dipping do not always yield the optimal, time-release dosage of the drugs delivered to the surrounding tissue. The drug or drug/polymer coating can include several layers such as the above drug-containing layer as well as a drug-free encapsulating layer, which can help to reduce the initial drug release amount caused by initial exposure to liquids when the device is first implanted.

A variety of methods have been employed to attach drugs or other therapeutic agents to an implantable medical device and to control the release rate of the drug/agent after surgical implantation. Barrier layers of polymers or co-polymers are added on top of the drugs to control the release rates of the attached drugs/agents and/or to control the rate of diffusion of external fluids (such as water or biological fluids) into the attached drugs. Drug/polymer mixtures are also employed in coating implantable medical devices. However, as previously explained, these polymers or co-polymers, while contributing to the control of the drug release rate, can have undesirable characteristics that reduce the overall medical success of the drug loaded implantable device and it is desirable that they could be completely eliminated.

Gas cluster ion beams have been employed to smooth or otherwise modify the surfaces of implantable medical devices such as stents and other implantable medical devices. For example, U.S. Pat. No. 6,676,989C1 issued to Kirkpatrick et al. teaches a GCIB processing system having a holder and manipulator suited for processing tubular or cylindrical workpieces such as vascular stents. In another example, U.S. Pat. No. 6,491,800B2 issued to Kirkpatrick et al. teaches a GCIB processing system having workpiece holders and manipulators for processing other types of non-planar medical devices, including for example, hip joint prostheses. In still another example, U.S. Pat. No. 7,105, 199B2 issued to Blinn et al. teaches the use of GCIB processing to improve the adhesion of drug coatings on stents and to modify the elution or release rate of the drug from the coatings. Ions have long been favored for many processes because their electric charge facilitates their manipulation by electrostatic and magnetic fields. This introduces great flexibility in processing. However, in some applications, the charge that is inherent to any ion (including gas cluster ions in a GCIB) may produce undesirable effects in the processed surfaces. GCIB has a distinct advantage over conventional ion beams in that a gas cluster ion with a single or small multiple charge enables the transport and control of a much larger mass-flow (a cluster may consist of hundreds or thousands of molecules) compared to a conventional ion (a single atom, molecule, or molecular fragment.) Particularly in the case of electrically insulating materials and materials having high electrical resistivity, such as the surfaces of many drug coatings or many polymers, or many drug-polymer mixtures, surfaces processed using ions often suffer from charge-induced damage resulting from abrupt discharge of accumulated charges, or production of damaging electrical field-induced stress in the material (again resulting from accumulated charges). In many such cases, GCIBs have an advantage due to their relatively low charge per mass, but in some instances may not eliminate the target-charging problem. Furthermore, moderate to high current intensity ion beams may suffer from a significant space charge-induced defocusing of the beam that tends to inhibit transporting a well-focused beam over long distances. Again, due to their lower charge per mass relative to conventional ion beams, GCIBs have an advantage, but they do not fully eliminate the space charge transport problem. Other needs/opportunities also exist as recognized and resolved through the present invention. In the field of drug-eluting medical implants, GCIB processing has been successful in treating surfaces of drug coatings on medical implants to bind the coating to a substrate or to modify the rate at which drugs are eluted from the coating following implantation into a patient. However, it has been noted that in some cases where GCIB has been used to process drug coatings (which are often very thin and may comprise very expensive drugs), there may occur a weight loss of the drug coating (indicative of drug loss or removal) as a result of the GCIB processing. For the particular cases where such loss occurs (certain drugs and using certain processing parameters) the occurrence is generally undesirable and having a process with the ability to avoid the weight loss, while still obtaining satisfactory control of the drug elution rate, is preferable. Since many drugs are electrically insulating materials, dielectric materials, or high electrical resistivity materials, they may be susceptible to damage by electrical charge. Such potential for damage may be reduced when accelerated Neutral Beams are used in place of gas cluster ion beams.

A further instance of need or opportunity arises from the fact that although the use of beams of neutral molecules or atoms provides benefit in some surface processing applications and in space charge-free beam transport, it has not generally been easy and economical to produce intense beams of neutral molecules or atoms except for the case of nozzle jets, where the energies are generally on the order of a few milli-electron-volts per atom or molecule, and thus have limited processing capabilities. More energetic neutral particles can be beneficial or necessary in many applications, for example when it is desirable to break surface or shallow subsurface bonds to facilitate cleaning, etching, smoothing, deposition, amorphization, or to produce surface chemistry effects. In such cases, energies of from about an eV up to a few thousands of eV per particle can often be useful. Methods and apparatus for forming such Neutral Beams by first forming an accelerated charged GCIB and then neutralizing or arranging for neutralization of at least a fraction of the beam and separating the charged and uncharged fractions are disclosed herein. The Neutral Beams may consist of neutral gas clusters, neutral monomers, or a combination of both. Although GCIB processing has been employed successfully for many applications, there are new and existing application needs, especially in relation to processing drug coatings for forming drug eluting medical devices, not fully met by GCIB or other state of the art methods and apparatus, and wherein accelerated Neutral Beams may provide superior results. For example, in many situations, while a GCIB can produce dramatic atomic-scale smoothing of an initially somewhat rough surface, the ultimate smoothing that can be achieved is often less than the required smoothness, and in other situations GCIB processing can result in roughening moderately smooth surfaces rather than smoothing them further.

In view of the importance of in situ drug delivery, it is desirable to have control over the drug release rate from the implantable device as well as control over other surface characteristics of the drug delivery medium and to accomplish such control without damage to the drug or any insulating materials or high electrical resistivity materials that may be present in the device.

It is therefore an object of this invention to provide a means of controlling surface characteristics of a drug eluting material using accelerated Neutral Beam technology.

It is a further object of this invention to improve the functional characteristics of known in situ drug release mechanisms using accelerated Neutral Beam technology.

Still another object of this invention is to provide a medical device that is a drug delivery system for delivering a quantity of a drug with temporal control of the drug delivery by employing barrier layers formed by irradiation with an accelerated Neutral Beam.

Still another object of this invention is to provide other devices that have coatings, wherein the release, evolution, or loss of the coating may be temporally controlled by employing barrier layers formed by irradiation of the coating material with an accelerated Neutral Beam.

SUMMARY OF THE INVENTION

The objects set forth above as well as further and other objects and advantages of the present invention are achieved by the invention described herein below. The present invention is directed to the use of Neutral Beam processing of materials (including drugs) attached to surfaces (including surfaces of medical devices intended for surgical implant) to modify and delay or otherwise improve the rate at which the materials are released from the surface (as for example by elution, evaporation, or sublimation). In the case of implantable drug coated medical devices, the release mechanism is normally by elution.

The present invention is directed to the use of accelerated Neutral Beam processing to modify the surface of drug or other coating to modify a surface layer of the drug or other coating material so as to control the rate at which the drug or material is released or eluted and/or to control the rate at which external fluids penetrate through the surface layer to the underlying drug, thereby eliminating the need for a polymer, co-polymer or any other binding agent and transforming the medical device surface into a drug delivery system. This will prevent the problem of toxicity and the damage caused by transportation of delaminated polymeric material throughout the body. Unlike the prior art stents that utilize a separately applied polymer barrier layer material or a drug-polymer (or co-polymer) mixture to control drug release or elution rate, the present invention provides the ability to completely avoid the use of a polymer or co-polymer binder or barrier layer in the preparation of a drug-releasing implantable medical device.

Beams of energetic conventional ions, accelerated electrically charged atoms or molecules, are widely utilized to form semiconductor device junctions, to modify surfaces by sputtering, and to modify the properties of thin films. Unlike conventional ions, gas cluster ions are formed from clusters of large numbers (having a typical distribution of several hundreds to several thousands with a mean value of a few thousand) of weakly bound atoms or molecules of materials that are gaseous under conditions of standard temperature and pressure (commonly oxygen, nitrogen, or an inert gas such as argon, for example, but any condensable gas can be used to generate gas cluster ions) with each cluster sharing one or more electrical charges, and which are accelerated together through large electric potential differences (on the order of from about 3 kV to about 70 kV or more) to have high total energies. After gas cluster ions have been formed and accelerated, their charge states may be altered or become altered (even neutralized) by collisions with other cluster ions, other neutral clusters, or residual background gas particles, and thus they may fragment or may be induced to fragment into smaller cluster ions or into monomer ions and/or into neutralized smaller clusters and neutralized monomers, but the resulting cluster ions, neutral clusters, and monomer ions and neutral monomers tend to retain the relatively high velocities and energies that result from having been accelerated through large electric potential differences, with the accelerated gas cluster ion energy being distributed over the fragments.

Because the energies of individual atoms within an energetic gas cluster ion are very small, typically a few eV to some tens of eV, the atoms penetrate through only a few atomic layers, at most, of a target surface during impact. This shallow penetration (typically a few nanometers to about ten nanometers, depending on the beam acceleration) of the impacting atoms means all of the energy carried by the entire cluster ion is consequently dissipated in an extremely small volume in the top surface layer during a time period less than a microsecond. This is different from using conventional ion beams where the penetration into the material is sometimes several hundred nanometers, producing changes deep below the surface of the material. Because of the high total energy of the gas cluster ion and extremely small interaction volume, the deposited energy density at the impact site is far greater than in the case of bombardment by conventional ions. For this reason, the GCIB or an accelerated Neutral Beam derived from a GCIB is capable of interacting with the surface of an organic material like a drug to produce profound changes in a very shallow surface layer of about 10 nanometers of less. Such changes may include cross linking of molecules, densification of the surface layer, carbonization of organic materials in the surface layer, polymerization, and other forms of denaturization.

As used herein, the terms "GCIB", "gas cluster ion beam" and "gas cluster ion" are intended to encompass not only ionized beams and ions, but also accelerated beams and ions that have had all or a portion of their charge states modified (including neutralized) following their acceleration. The terms "GCIB" and "gas cluster ion beam" are intended to encompass all beams that comprise accelerated gas cluster ions even though they may also comprise non-clustered particles. As used herein, the term "Neutral Beam" is intended to mean a beam of neutral gas clusters and/or neutral monomers derived from an accelerated gas cluster ion beam and wherein the acceleration results from acceleration of a gas cluster ion beam. As used herein, the term "monomer" refers equally to either a single atom or a single molecule. The terms "atom," "molecule," and "monomer" may be used interchangeably and all refer to the appropriate monomer that is characteristic of the gas under discussion (either a component of a cluster, a component of a cluster ion, or an atom or molecule). For example, a monatomic gas like argon may be referred to in terms of atoms, molecules, or monomers and each of those terms means a single atom. Likewise, in the case of a diatomic gas like nitrogen, it may be referred to in terms of atoms, molecules, or monomers, each term meaning a diatomic molecule. Furthermore a molecular gas like $CO_2$, may be referred to in terms of atoms, molecules, or monomers, each term meaning a three atom molecule, and so forth. These conventions are used to simplify generic discussions of gases and gas clusters or gas cluster ions independent of whether they are monatomic, diatomic, or molecular in their gaseous form.

As used herein, the term "drug" is intended to mean a therapeutic agent or a material that is active in a generally beneficial way, which can be released or eluted locally in the vicinity of an implantable medical device to facilitate implanting (for example, without limitation, by providing lubrication) the device, or to facilitate (for example, without limitation, through biological or biochemical activity) a favorable medical or physiological outcome of the implantation of the device. "Drug" is not intended to mean a mixture of a drug with a polymer that is employed for the purpose of binding or providing coherence to the drug, attaching the drug to the medical device, or for forming a barrier layer to control release or elution of the drug. A drug that has been modified by beam irradiation to densify, carbonize or partially carbonize, partially denature, cross-link or partially cross-link, or to at least partially polymerize molecules of the drug is intended to be included in the "drug" definition. As used herein, the term "polymer" is intended to include co-polymers and to mean a material that is significantly polymerized and which is not biologically active in a generally beneficial way in either its monomer or polymer form. Typical polymers may include, without limitation, polylactic acid, polyglycolic acid, polylactic-co-glycolic acid, polylactic acid-co-caprolactone, polyethylene glycol, polyethylene oxide, polyvinyl pyrrolidone, polyorthoesters, polysaccharides, polysaccharide derivatives, polyhyaluronic acid, polyalginic acid, chitin, chitosan, various celluloses, polypeptides, polylysine, polyglutamic acid, polyanhydrides, polyhydroxy alkonoates, polyhydroxy valerate, polyhydroxy butyrate, and polyphosphate esters. The term "polymer" is not intended to include a drug that has been modified by beam irradiation to densify, carbonize or partially carbonize, partially denature, cross-link or partially cross-link, or to at least partially polymerize molecules of the drug.

As used herein, the term "elution" is intended to mean the release of an at least somewhat soluble drug material from a drug source on a medical device or in a hole in a medical device by gradual solution of the drug in a solvent, typically a bodily fluid solvent encountered after implantation of the medical device in a subject. In many cases the solubility of a drug material is high enough that the release of the drug into solution occurs more rapidly than desired, undesirably shortening the therapeutic lifetime of the drug following implantation of the medical device. The rate of elution or rate of release of the drug may depend on many factors such as for examples, solubility of the drug or exposed surface area between the drug and the solvent or mixture of the drug with other materials to reduce solubility. However, barrier or encapsulating layers between the drug and solvent can also modify the rate of elution or release of the drug. It is often desirable to delay the rate of release by elution to extend the time of therapeutic influence at the implant site. The desired elution rates are well known per se to those working in the arts of the medical devices. The present invention enhances their control of those rates in the devices. See, e.g. http://www.news-medical.net/health/Drug-Eluting-Stent-Design.aspx (duration of elution). U.S. Pat. No. 3,641,237 teaches some specific drug elution rates. Haery et al., "Drug-eluting stents: The beginning of the end of restenosis?", Cleveland Clinic Journal of Medicine, V71(10), (2004), includes some details of drug release rates for stents at pg. 818, Col. 2, paragraph 5. As used herein, the term "diffusion" is intended to mean the concentration gradient driven transport of a material across or through a barrier layer. A fluid (such as a biological fluid) diffusing across a barrier layer typically results in a molecular scale movement from the side on which the fluid is more abundant to the side where it is less abundant, with a resulting concentration gradient within the layer.

When accelerated gas cluster ions are fully dissociated and neutralized, the resulting neutral monomers will have energies approximately equal to the total energy of the original accelerated gas cluster ion, divided by the number, NI, of monomers that comprised the original gas cluster ion at the time it was accelerated. Such dissociated neutral monomers will have energies on the order of from about 1 eV to tens or even as much as a few thousands of eV, depending on the original accelerated energy of the gas cluster ion and the size of the gas cluster at the time of acceleration.

Gas cluster ion beams are generated and transported for purposes of irradiating a workpiece according to known techniques. Various types of holders are known in the art for holding the object in the path of the GCIB for irradiation and for manipulating the object to permit irradiation of a multiplicity of portions of the object. Neutral Beams may be generated and transported for purposes of irradiating a workpiece according to techniques taught herein.

The present invention may employ a high beam purity method and system for deriving from an accelerated gas cluster ion beam an accelerated neutral gas cluster and/or preferably monomer beam that can be employed for a variety of types of surface and shallow subsurface materials processing and which is capable, for many applications, of superior performance compared to conventional GCIB processing. It can provide well-focused, accelerated, intense neutral monomer beams with particles having energies in the range of from about 1 eV to as much as a few thousand eV. This is an energy range in which it has heretofore been impractical with simple, relatively inexpensive apparatus to form intense neutral beams.

These accelerated Neutral Beams are generated by first forming a conventional accelerated GCIB, then partly or essentially fully dissociating it by methods and operating conditions that do not introduce impurities into the beam, then separating the remaining charged portions of the beam from the neutral portion, and subsequently using the resulting accelerated Neutral Beam for workpiece processing. Depending on the degree of dissociation of the gas cluster ions, the Neutral Beam produced may be a mixture of neutral gas monomers and gas clusters or may essentially consist entirely or almost entirely of neutral gas monomers. It is preferred that the accelerated Neutral Beam is a fully dissociated neutral monomer beam.

An advantage of the Neutral Beams that may be produced by the methods and apparatus of this invention, is that they may be used to process electrically insulating materials without producing damage to the material due to charging of the surfaces of such materials by beam transported charges as commonly occurs for all ionized beams including GCIB. For example, in semiconductor and other electronic applications, ions often contribute to damaging or destructive charging of thin dielectric films such as oxides, nitrides, etc. The use of Neutral Beams can enable successful beam processing of polymer, dielectric, and/or other electrically insulating or high electrical resistivity materials, coatings, and films in other applications where ion beams may produce undesired side effects due to surface or other charging effects. Examples include (without limitation) processing of corrosion inhibiting coatings, and irradiation cross-linking and/or polymerization of organic films. In other examples, Neutral Beam induced modifications of polymer or other dielectric materials (e.g. sterilization, smoothing, improving surface biocompatibility, and improving attachment of and/or control of elution rates of drugs) may enable the use of such materials in medical devices for implant and/or other medical/surgical applications. Further examples include Neutral Beam processing of glass, polymer, and ceramic bio-culture labware and/or environmental sampling surfaces where such beams may be used to improve surface characteristics like, for example, roughness, smoothness, hydrophilicity, and biocompatibility.

Since the parent GCIB, from which accelerated Neutral Beams may be formed by the methods and apparatus of the invention, comprises ions it is readily accelerated to desired energy and is readily focused using conventional ion beam techniques. Upon subsequent dissociation and separation of the charged ions from the neutral particles, the neutral beam particles tend to retain their focused trajectories and may be transported for extensive distances with good effect.

When neutral gas clusters in a jet are ionized by electron bombardment, they become heated and/or excited. This may result in subsequent evaporation of monomers from the ionized gas cluster, after acceleration, as it travels down the beamline. Additionally, collisions of gas cluster ions with background gas molecules in the ionizer, accelerator and beamline regions, also heat and excite the gas cluster ions and may result in additional subsequent evolution of monomers from the gas cluster ions following acceleration. When these mechanisms for evolution of monomers are induced by electron bombardment and/or collision with background gas molecules (and/or other gas clusters) of the same gas from which the GCIB was formed, no contamination is contributed to the beam by the dissociation processes that results in evolving the monomers.

There are other mechanisms that can be employed for dissociating (or inducing evolution of monomers from) gas cluster ions in a GCIB without introducing contamination into the beam. Some of these mechanisms may also be employed to dissociate neutral gas clusters in a neutral gas cluster beam. One mechanism is laser irradiation of the cluster-ion beam using infra-red or other laser energy. Laser-induced heating of the gas cluster ions in the laser irradiated GCIB results in excitement and/or heating of the gas cluster ions and causes subsequent evolution of monomers from the beam. Another mechanism is passing the beam through a thermally heated tube so that radiant thermal energy photons impact the gas cluster ions in the beam. The induced heating of the gas cluster ions by the radiant thermal energy in the tube results in excitement and/or heating of the gas cluster ions and causes subsequent evolution of monomers from the beam. In another mechanism, crossing the gas cluster ion beam by a gas jet of the same gas or mixture as the source gas used in formation of the GCIB (or other non-contaminating gas) results in collisions of monomers of the gas in the gas jet with the gas clusters in the ion beam producing excitement and/or heating of the gas cluster ions in the beam and subsequent evolution of monomers from the excited gas cluster ions. By depending entirely on electron bombardment during initial ionization and/or collisions (with other cluster ions, or with background gas molecules of the same gas(es) as those used to form the GCIB) within the beam and/or laser or thermal radiation and/or crossed jet collisions of non-contaminating gas to produce the GCIB dissociation and/or fragmentation, contamination of the beam by collision with other materials is avoided.

As a neutral gas cluster jet from a nozzle travels through an ionizing region where electrons are directed to ionize the clusters, a cluster may remain un-ionized or may acquire a charge state, q, of one or more charges (by ejection of electrons from the cluster by an incident electron). The ionizer operating conditions influence the likelihood that a gas cluster will take on a particular charge state, with more intense ionizer conditions resulting in greater probability that a higher charge state will be achieved. More intense ionizer conditions resulting in higher ionization efficiency may result from higher electron flux and/or higher (within limits) electron energy. Once the gas cluster has been ionized, it is typically extracted from the ionizer, focused into a beam, and accelerated by falling through an electric field. The amount of acceleration of the gas cluster ion is readily controlled by controlling the magnitude of the accelerating electric field. Typical commercial GCIB processing tools generally provide for the gas cluster ions to be accelerated by an electric field having an adjustable accelerating potential, VAcc, typically of, for example, from about 1 kV to 70 kV (but not limited to that range—VAcc up to 200 kV or even more may be feasible). Thus a singly charged gas cluster ion achieves an energy in the range of from 1 to 70 keV (or more if larger VAcc is used) and a multiply charged (for example, without limitation, charge state, q=3 electronic charges) gas cluster ion achieves an energy in the range of from 3 to 210 keV (or more for higher VAcc). For other gas cluster ion charge states and acceleration potentials, the accelerated energy per cluster is qVAcc eV. From a given ionizer with a given ionization efficiency, gas cluster ions will have a distribution of charge states from zero (not ionized) to a higher number such as for example 6 (or with high ionizer efficiency, even more), and the most probable and mean values of the charge state distribution also increase with increased ionizer efficiency (higher electron flux and/or energy). Higher ionizer efficiency also results in increased numbers of gas cluster ions being formed in the ionizer. In many cases, GCIB processing throughput increases when operating the ionizer at high efficiency results in increased GCIB current. A downside of such operation is that multiple charge states that may occur on intermediate size gas cluster ions can increase crater and/or rough interface formation by those ions, and often such effects may operate counterproductively to the intent of the processing. Thus for many GCIB surface processing recipes, selection of the ionizer operating parameters tends to involve more considerations than just maximizing beam current. In some processes, use of a "pressure cell" (see U.S. Pat. No. 7,060,989, to Swenson et al.) may be employed to permit operating an ionizer at high ionization efficiency while still obtaining acceptable beam processing performance by moderating the beam energy by gas collisions in an elevated pressure "pressure cell."

With the present invention there is no downside to operating the ionizer at high efficiency—in fact such operation is sometimes preferred. When the ionizer is operated at high efficiency, there may be a wide range of charge states in the gas cluster ions produced by the ionizer. This results in a wide range of velocities in the gas cluster ions in the extraction region between the ionizer and the accelerating electrode, and also in the downstream beam. This may result in an enhanced frequency of collisions between and among gas cluster ions in the beam that generally results in a higher degree of fragmentation of the largest gas cluster ions. Such fragmentation may result in a redistribution of the cluster sizes in the beam, skewing it toward the smaller cluster sizes. These cluster fragments retain energy in proportion to their new size (N) and so become less energetic while essentially retaining the accelerated velocity of the initial unfragmented gas cluster ion. The change of energy with retention of velocity following collisions has been experimentally verified (as for example reported in Toyoda, N. et al., "Cluster size dependence on energy and velocity distributions of gas cluster ions after collisions with residual gas," Nucl. Instr. & Meth. in Phys. Research B 257 (2007), pp 662-665). Fragmentation may also result in redistribution of charges in the cluster fragments. Some uncharged fragments likely result and multi-charged gas cluster ions may fragment into several charged gas cluster ions and perhaps some uncharged fragments. It is understood by the inventors that design of the focusing fields in the ionizer and the extraction region may enhance the focusing of the smaller gas cluster ions and monomer ions to increase the likelihood of collision with larger gas cluster ions in the beam extraction region and in the downstream beam, thus contributing to the dissociation and/or fragmenting of the gas cluster ions.

In an embodiment of the present invention, background gas pressure in the ionizer, acceleration region, and beamline may optionally be arranged to have a higher pressure than is normally utilized for good GCIB transmission. This can result in additional evolution of monomers from gas cluster ions (beyond that resulting from the heating and/or excitement resulting from the initial gas cluster ionization event). Pressure may be arranged so that gas cluster ions have a short enough mean-free-path and a long enough flight path between ionizer and workpiece that they must undergo multiple collisions with background gas molecules.

For a homogeneous gas cluster ion containing N monomers and having a charge state of q and which has been accelerated through an electric field potential drop of VAcc volts, the cluster will have an energy of approximately qVAcc/NI eV per monomer, where NI is the number of monomers in the cluster ion at the time of acceleration. Except for the smallest gas cluster ions, a collision of such an ion with a background gas monomer of the same gas as the cluster source gas will result in additional deposition of approximately qVAcc/NI eV into the gas cluster ion. This energy is relatively small compared to the overall gas cluster ion energy (qVAcc) and generally results in excitation or heating of the cluster and in subsequent evolution of monomers from the cluster. It is believed that such collisions of larger clusters with background gas seldom fragment the cluster but rather heats and/or excites it to result in evolution of monomers by evaporation or similar mechanisms.

Regardless of the source of the excitation that results in the evolution of a monomer or monomers from a gas cluster ion, the evolved monomer(s) have approximately the same energy per particle, qVAcc/NI eV, and retain approximately the same velocity and trajectory as the gas cluster ion from which they have evolved. When such monomer evolutions occur from a gas cluster ion, whether they result from excitation or heating due to the original ionization event, a collision, or radiant heating, the charge has a high probability of remaining with the larger residual gas cluster ion. Thus after a sequence of monomer evolutions, a large gas cluster ion may be reduced to a cloud of co-traveling monomers with perhaps a smaller residual gas cluster ion (or possibly several if fragmentation has also occurred). The co-traveling monomers following the original beam trajectory all have approximately the same velocity as that of the original gas cluster ion and each has energy of approximately qVAcc/NI eV. For small gas cluster ions, the energy of collision with a background gas monomer is likely to completely and violently dissociate the small gas cluster and it is uncertain whether in such cases the resulting monomers continue to travel with the beam or are ejected from the beam.

Prior to the GCIB reaching the workpiece, the remaining charged particles (gas cluster ions, particularly small and intermediate size gas cluster ions and some charged monomers, but also including any remaining large gas cluster ions) in the beam are separated from the neutral portion of the beam, leaving only a Neutral Beam for processing the workpiece.

In typical operation, the fraction of power in the neutral beam components relative to that in the full (charged plus neutral) beam delivered at the processing target is in the range of from about 5% to 95%, so by the separation methods and apparatus of the present invention it is possible to deliver that portion of the kinetic energy of the full accelerated charged beam to the target as a Neutral Beam.

The dissociation of, the gas cluster ions and thus the production of high neutral monomer beam energy is facilitated by 1) Operating at higher acceleration voltages. This increases qVAcc/N for any given cluster size. 2) Operating at high ionizer efficiency. This increases qVAcc/N for any given cluster size by increasing q and increases cluster-ion on cluster-ion collisions in the extraction region due to the differences in charge states between clusters; 3) Operating at a high ionizer, acceleration region, or beamline pressure or operating with a gas jet crossing the beam, or with a longer beam path, all of which increase the probability of background gas collisions for a gas cluster ion of any given size; 4) Operating with laser irradiation or thermal radiant heating of the beam, which directly promote evolution of monomers from the gas cluster ions; and 5) Operating at higher nozzle gas flow, which increases transport of gas, clustered and perhaps unclustered into the GCIB trajectory, which increases collisions resulting in greater evolution of monomers.

Measurement of the Neutral Beam cannot be made by current measurement as is convenient for gas cluster ion beams. A Neutral Beam power sensor is used to facilitate dosimetry when irradiating a workpiece with a Neutral Beam. The Neutral Beam sensor is a thermal sensor that intercepts the beam (or optionally a known sample of the beam). The rate of rise of temperature of the sensor is related to the energy flux resulting from energetic beam irradiation of the sensor. The thermal measurements must be made over a limited range of temperatures of the sensor to avoid errors due to thermal re-radiation of the energy incident on the sensor. For a GCIB process, the beam power (watts) is equal to the beam current (amps) times VAcc, the beam acceleration voltage. When a GCIB irradiates a workpiece for a period of time (seconds), the energy (joules) received by the workpiece is the product of the beam power and the irradiation time. The processing effect of such a beam when it processes an extended area is distributed over the area (for example, cm2). For ion beams, it has been conveniently conventional to specify a processing dose in terms of irradiated ions/cm2, where the ions are either known or assumed to have at the time of acceleration an average charge state, q, and to have been accelerated through a potential difference of, VAcc volts, so that each ion carries an energy of q VAcc eV (an eV is approximately $1.6 \times 10{-}19$ joule). Thus an ion beam dose for an average charge state, q, accelerated by VAcc and specified in ions/cm2 corresponds to a readily calculated energy dose expressible in joules/cm2. For an accelerated Neutral Beam derived from an accelerated GCIB as utilized in the present invention, the value of q at the time of acceleration and the value of VAcc is the same for both of the (later-formed and separated) charged and uncharged fractions of the beam. The power in the two (neutral and charged) fractions of the GCIB divides proportionally to the mass in each beam fraction. Thus for the accelerated Neutral Beam as employed in the invention, when equal areas are irradiated for equal times, the energy dose (joules/cm2) deposited by the Neutral Beam is necessarily less than the energy dose deposited by the full GCIB. By using a thermal sensor to measure the power in the full GCIB PG and that in the Neutral Beam PN (which is commonly found to be about 5% to 95% that of the full GCIB) it is possible to calculate a compensation factor for use in the Neutral Beam processing dosimetry. When PN is aPG, then the compensation factor is, k=1/a. Thus if a workpiece is processed using a Neutral Beam derived from a GCIB, for a time duration is made to be k times greater than the processing duration for the full GCIB (including charged and neutral beam portions) required to achieve a dose of D ions/cm2, then the energy doses deposited in the workpiece by both the Neutral Beam and the full GCIB are the same (though the results may be different due to qualitative differences in the processing effects due to differences of particle sizes in the two beams.) As used herein, a Neutral Beam process dose compensated in this way is sometimes described as having an energy/cm2 equivalence of a dose of D ions/cm2.

Use of a Neutral Beam derived from a gas cluster ion beam in combination with a thermal power sensor for dosimetry in many cases has advantages compared with the use of the full gas cluster ion beam or an intercepted or diverted portion, which inevitably comprises a mixture of gas cluster ions and neutral gas clusters and/or neutral monomers, and which is conventionally measured for dosimetry purposes by using a beam current measurement. Some advantages are as follows:

1) The dosimetry can be more precise with the Neutral Beam using a thermal sensor for dosimetry because the total power of the beam is measured. With a GCIB employing the traditional beam current measurement for dosimetry, only the contribution of the ionized portion of the beam is measured and employed for dosimetry. Minute-to-minute and setup-to-setup changes to operating conditions of the GCIB apparatus may result in variations in the fraction of neutral monomers and neutral clusters in the GCIB. These variations can result in process variations that may be less controlled when the dosimetry is done by beam current measurement.

2) With a Neutral Beam, any material may be processed, including highly insulating materials and other materials that may be damaged by electrical charging effects, without the necessity of providing a source of target neutralizing electrons to prevent workpiece charging due to charge transported to the workpiece by an ionized beam. When employed with conventional GCIB, target neutralization to reduce charging is seldom perfect, and the neutralizing electron source itself often introduces problems such as workpiece heating, contamination from evaporation or sputtering in the electron source, etc. Since a Neutral Beam does not transport charge to the workpiece, such problems are reduced.

3) There is no necessity for an additional device such as a large aperture high strength magnet to separate energetic monomer ions from the Neutral Beam. In the case of conventional GCIB the risk of energetic monomer ions (and other small cluster ions) being transported to the workpiece, where they penetrate producing deep damage, is significant and an expensive magnetic filter is routinely required to separate such particles from the beam. In the case of the Neutral Beam apparatus of the invention, the separation of all ions from the beam to produce the Neutral Beam inherently removes all monomer ions.

The application of the drug(s) to the medical device may be accomplished by several methods. The surface of the medical device, which may be composed, for example, of a metal, metal alloy, ceramic, or many other materials, is first processed to form one or more holes in the surface thereof. The desired drug(s) is then deposited into the holes. The drug deposition may be by any of numerous methods, including spraying, dipping, electrostatic deposition, ultrasonic spraying, vapor deposition, or by discrete droplet-on-demand fluid jetting technology. When spraying, dipping, electrostatic deposition, ultrasonic spraying, vapor deposition, or similar techniques are employed, a conventional masking scheme may be employed to limit deposition to selected locations. Discrete droplet-on-demand fluid-jetting is a preferred method because it provides the ability to introduce precise volumes of liquid drugs or drugs-in-solution into precisely programmable locations. Discrete droplet-on-demand fluid jetting may be accomplished using commercially available fluid-jet print head jetting devices as are available (for example, not limitation) from MicroFab Technologies, Inc., of Plano, Tex.

After the devices have been drug-loaded, the present invention uses accelerated Neutral Beam irradiation, to modify a very shallow surface layer of the retained drug to alter the drug in that layer in a way that modifies its properties in a way that forms a thin surface film with barrier properties that limit diffusion across the surface film. This results in the ability to control the rate of diffusion of water or other biological fluids into the drug retained in the hole, and to control the rate of elution of the drug out from the hole. The modification of the surface portion of the drug that becomes the surface film having barrier properties may consist of any of several modification outcomes, depending on the nature of the drug and the parameters of the accelerated Neutral Beam processing. Possible outcomes include cross-linking or polymerizing of the drug molecules, carbonization of the drug material by driving out more volatile atoms from the molecules, densification of the drug, and other forms of denaturization that result in reduced solubility, erodibility, and/or in reduced porosity or diffusion rates.

In addition to simple coating of medical devices with drugs, in some situations, stents and other medical devices utilize cavities (holes) to contain larger quantities of drugs. In such cases barrier layers formed on the surfaces of the contained drugs also benefit from formation by irradiation with accelerated Neutral Beam irradiation, and eliminate the need (and possible adverse side effects) of adding additional materials such as polymer caps or barrier layers to retain the drugs and modify or delay elution characteristics. In exemplary embodiments described herein where the use of holes is described for retaining drugs, it should be understood, that the same principles of barrier layer formation using accelerated Neutral Beams are equally applicable to simple coatings on flat surfaces.

One embodiment of the present invention provides a medical device having a surface adapted for delivering one or more drugs, comprising: and one or more drug coating layers on the surface of the device, at least one of the drug coating layers having at least one barrier layer adapted for controlling a rate of flow of material across the at least one barrier layer, and further wherein the at least one barrier layer consists of drug modified by Neutral Beam irradiation. The at least one barrier layer may control a release rate of drugs; control an elution rate of drugs; or control an inward diffusion rate of a fluid into at least one of the one or more drug coating layers.

At least one drug coating layer of the one or more drug coating layers may contain a first quantity of a first drug, the first drug overlaid by a first barrier layer comprising modified first drug, the first barrier layer overlaid by a second quantity of a second drug, the second drug overlaid by a second barrier layer comprising modified second drug. The first drug and the second drug may be the same drug or different drugs; and the first barrier layer and the second barrier layer may be constructed to control a temporal release profile of the first and second drugs. The controlled flow rate may be: a drug elution rate; a drug release rate; or a fluid diffusion rate. The medical device may be any of: a vascular stent; a coronary stent; an artificial joint prosthesis; an artificial joint prosthesis component; or a coronary pacemaker. The at least one barrier layer may comprise modified drug is selected from the group consisting of: cross-linked drug molecules; a densified drug; a carbonized organic drug material; a polymerized drug; or a denaturized drug; and combinations thereof. The at least one barrier layer may comprise a biologically active material.

Another embodiment of the present invention provides a method of modifying a surface of a medical device comprising the steps: a. depositing a first drug coating layer on at least a portion of the surface of the medical device; b. optionally depositing one or more additional drug coating layers on the first drug coating layer to form a plurality of drug coating layers; c. forming an accelerated Neutral Beam; and d. irradiating a first exposed surface of at least one of the first drug coating layer or any additional drug coating layer with the Neutral Beam to form a barrier layer at the first exposed surface.

The method may further comprise the steps, prior to the depositing step a.: forming a second beam; and second irradiating at least a portion of the surface of the medical device with the second beam to: clean the at least a portion of the surface of the medical device; smooth the at least a portion of the surface of the medical device; or remove a sharp or burred edge on the at least a portion of the surface of the medical device. The irradiating step d. may form the barrier layer by modifying the drug at the exposed surface by: cross-linking molecules of the drug; densifying the drug; carbonizing the drug; polymerizing the drug; or denaturing the drug. The barrier layer may control a rate of inward diffusion of a fluid into the drug coating. The barrier layer may control a rate of outward elution of drug from the drug coating. The Neutral Beam may be derived from an accelerated gas cluster ion beam. A first drug coating layer and an additional drug coating layer may comprise different drug materials.

The method may comprise the additional steps forming a third beam and irradiating a second exposed surface of at least one of the first drug coating layer or any additional drug coating layer with the third beam to form a second barrier layer at the second exposed surface. The third beam may be a Neutral Beam. The third beam may be a gas cluster ion beam. The first barrier layer and the second barrier layer may have different properties for differently controlling elution rates of two drug coating layers.

BRIEF DESCRIPTION OF THE DRAWINGS

For a better understanding of the present invention, together with other and further objects thereof, reference is made to the accompanying drawings, wherein.

DETAILED DESCRIPTION OF THE PREFERRED EMBODIMENTS

Figure 1A:
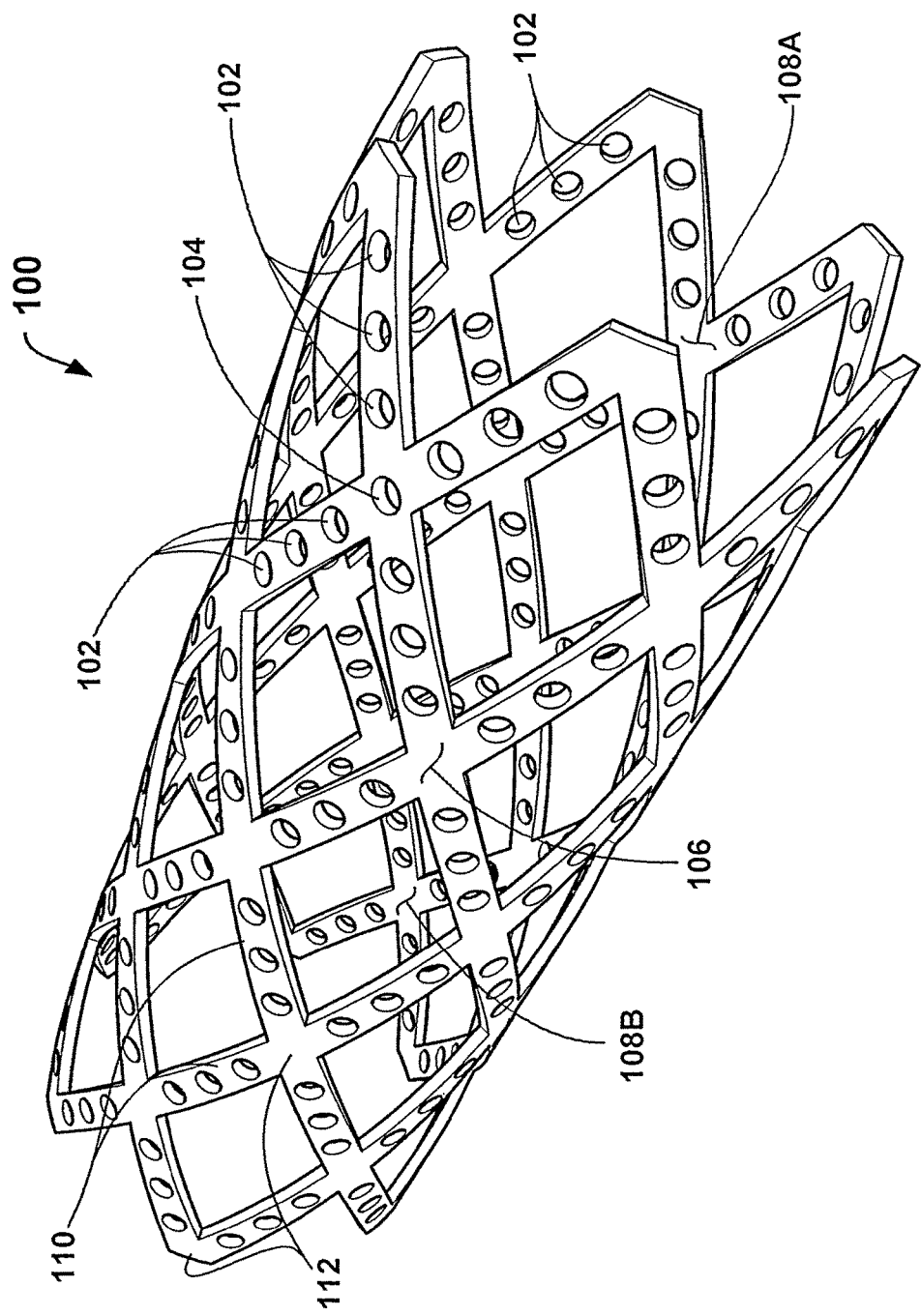
FIG. 1A is a coronary stent with through-holes as may be employed in embodiments of the invention.
Figure 1B:
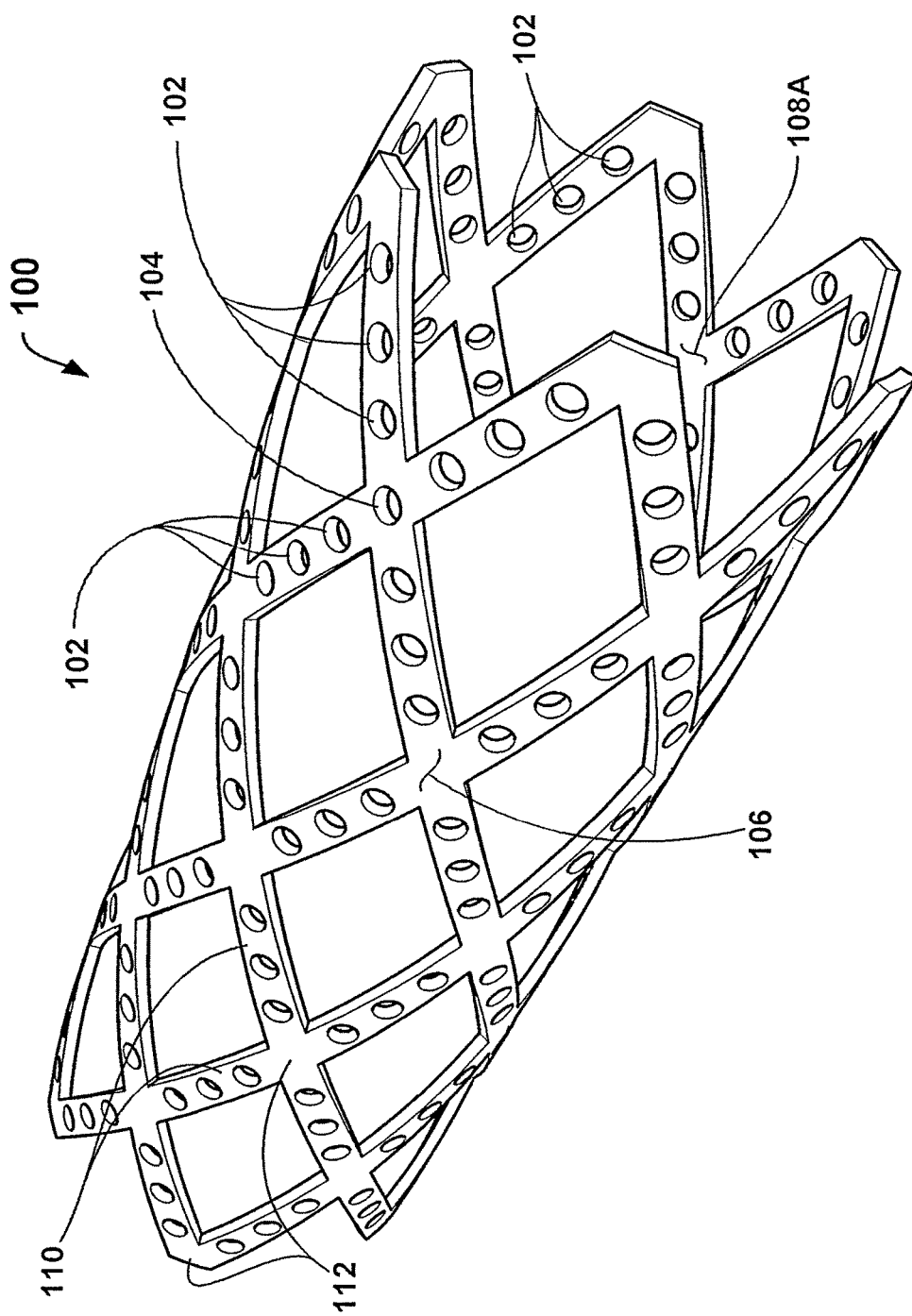
FIG. 1B is a second view of the coronary stent simplified for clarity by removal of detail beyond the nearest surface.
Figure 2:
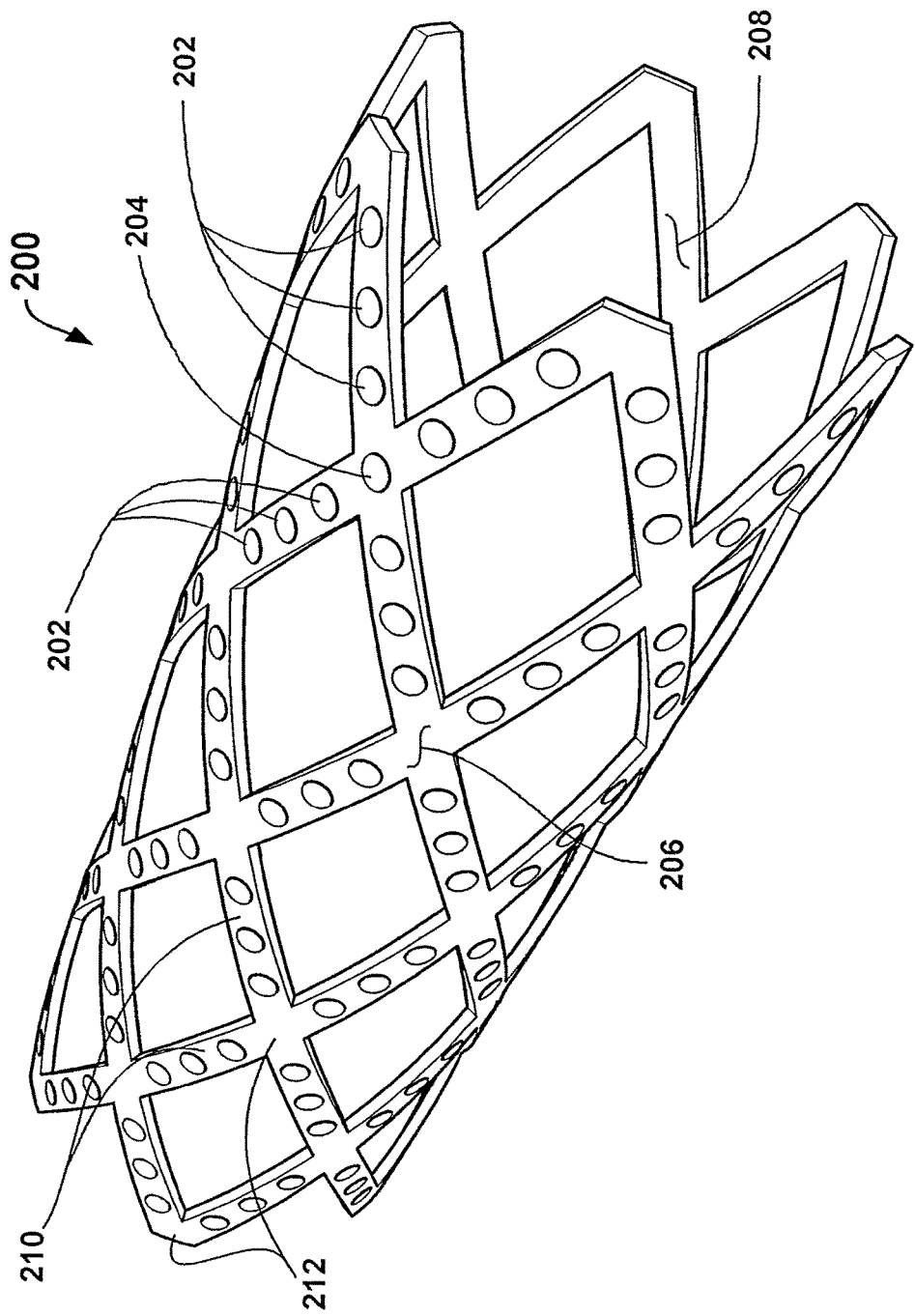
FIG. 2 is a view of coronary stent with blind-holes as may be employed in embodiments of the invention.

In the following description, for simplification, item numbers from earlier-described figures may appear in subsequently-described figures without discussion. Likewise, items discussed in relation to earlier figures may appear in subsequent figures without item numbers or additional description. In such cases items with like numbers are like items and have the previously-described features and functions, and illustration of items without item numbers shown in the present figure refer to like items having the same functions as the like items illustrated in earlier-discussed numbered figures.

In an embodiment of the invention, a Neutral Beam derived from an accelerated gas cluster ion beam is employed to process insulating (and other sensitive) surfaces.

Beams of energetic ions, electrically charged atoms or molecules accelerated through high voltages under vacuum, are widely utilized to form semiconductor device junctions, to smooth surfaces by sputtering, and to enhance the properties of semiconductor thin films. In the present invention, these same beams of energetic ions are utilized for affecting surface characteristics of drug eluting medical devices, such as, for example, coronary stents, thereby enhancing the drug delivery properties and the bio-compatibility of such drug delivery systems.

In the preferred embodiment of the present invention, gas cluster ion beam GCIB processing is utilized. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important micro-scale surface effects possible that are not possible in any other way.

The concept of GCIB processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual sub-surface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of 10-12 seconds (i.e. one picosecond). This is different from the case of ion implantation, which is normally done with conventional monomer ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional monomer ions.

Figure 7:
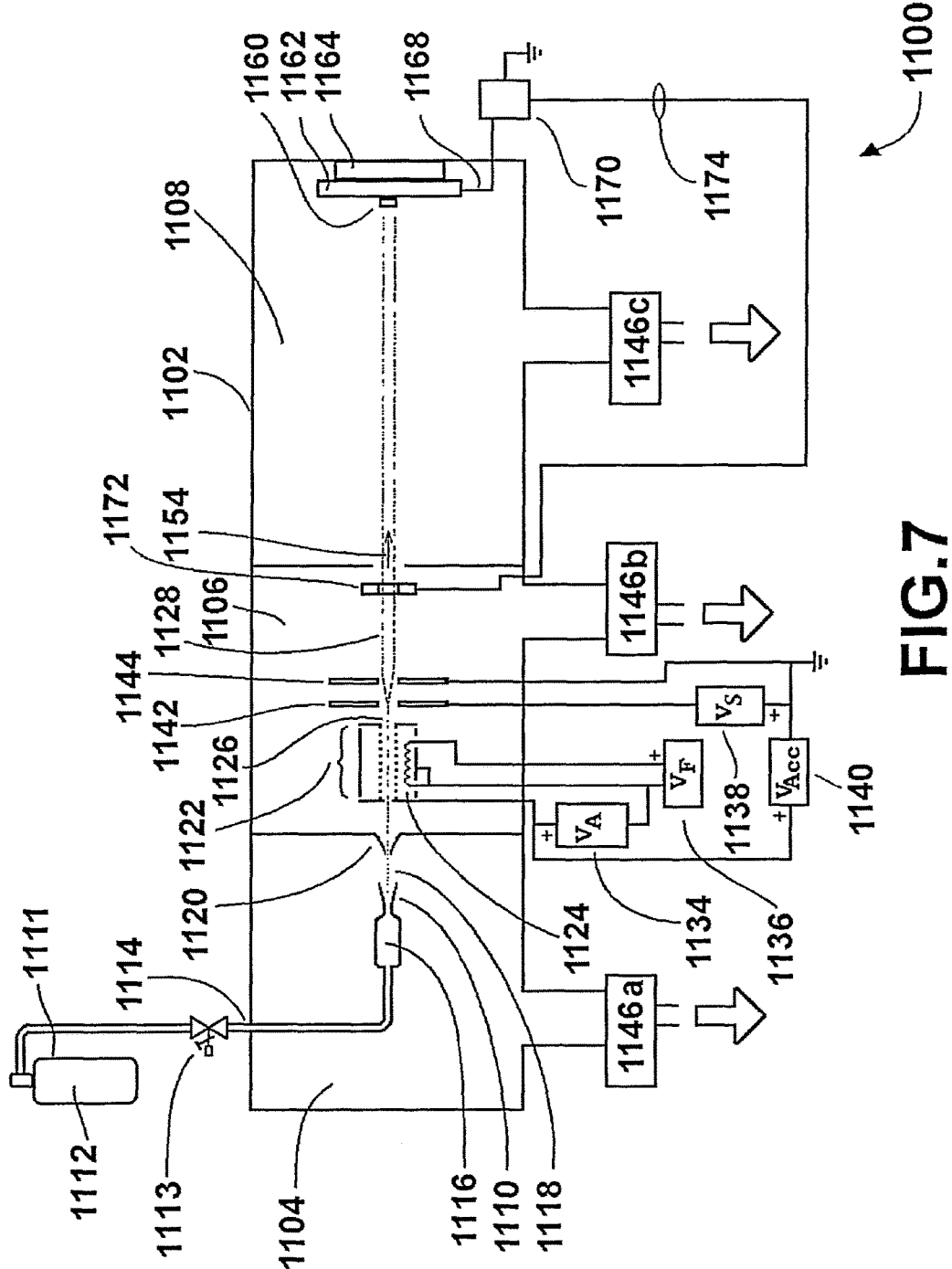
FIG. 7 is a schematic illustrating elements of a GCIB processing apparatus 1100 for processing a workpiece using a GCIB.

Reference is now made to FIG. 7, which shows a schematic configuration for a GCIB processing apparatus 1100. A low-pressure vessel 1102 has three fluidly connected chambers: a nozzle chamber 1104, an ionization/acceleration chamber 1106, and a processing chamber 1108. The three chambers are evacuated by vacuum pumps 1146a, 1146b, and 1146c, respectively. A pressurized condensable source gas 1112 (for example argon) stored in a gas storage cylinder 1111 flows through a gas metering valve 1113 and a feed tube 1114 into a stagnation chamber 1116. Pressure (typically a few atmospheres) in the stagnation chamber 1116 results in ejection of gas into the substantially lower pressure vacuum through a nozzle 1110, resulting in formation of a supersonic gas jet 1118. Cooling, resulting from the expansion in the jet, causes a portion of the gas jet 1118 to condense into clusters, each consisting of from several to several thousand weakly bound atoms or molecules. A gas skimmer aperture 1120 is employed to control flow of gas into the downstream chambers by partially separating gas molecules that have not condensed into a cluster jet from the cluster jet. Excessive pressure in the downstream chambers can be detrimental by interfering with the transport of gas cluster ions and by interfering with management of the high voltages that may be employed for beam formation and transport. Suitable condensable source gases 1112 include, but are not limited to argon and other condensable noble gases, nitrogen, carbon dioxide, oxygen, and many other gases and/or gas mixtures. After formation of the gas clusters in the supersonic gas jet 1118, at least a portion of the gas clusters are ionized in an ionizer 1122 that is typically an electron impact ionizer that produces electrons by thermal emission from one or more incandescent filaments 1124 (or from other suitable electron sources) and accelerates and directs the electrons, enabling them to collide with gas clusters in the gas jet 1118. Electron impacts with gas clusters eject electrons from some portion of the gas clusters, causing those clusters to become positively ionized. Some clusters may have more than one electron ejected and may become multiply ionized. Control of the number of electrons and their energies after acceleration typically influences the number of ionizations that may occur and the ratio between multiple and single ionizations of the gas clusters. A suppressor electrode 1142, and grounded electrode 1144 extract the cluster ions from the ionizer exit aperture 1126, accelerate them to a desired energy (typically with acceleration potentials of from several hundred V to several tens of kV), and focuses them to form a GCIB 1128. The region that the GCIB 1128 traverses between the ionizer exit aperture 126 and the suppressor electrode 1142 is referred to as the extraction region. The axis (determined at the nozzle 1110), of the supersonic gas jet 1118 containing gas clusters is substantially the same as the axis 1154 of the GCIB 1128. Filament power supply 1136 provides filament voltage Vf to heat the ionizer filament 1124. Anode power supply 1134 provides anode voltage VA to accelerate thermoelectrons emitted from filament 1124 to cause the thermoelectrons to irradiate the cluster-containing gas jet 1118 to produce cluster ions. A suppression power supply 1138 supplies suppression voltage VS (on the order of several hundred to a few thousand volts) to bias suppressor electrode 1142. Accelerator power supply 1140 supplies acceleration voltage VAcc to bias the ionizer 1122 with respect to suppressor electrode 1142 and grounded electrode 1144 so as to result in a total GCIB acceleration potential equal to VAcc. Suppressor electrode 1142 serves to extract ions from the ionizer exit aperture 1126 of ionizer 1122 and to prevent undesired electrons from entering the ionizer 1122 from downstream, and to form a focused GCIB 1128.

A workpiece 1160, which may (for example) be a medical device, a semiconductor material, an optical element, or other workpiece to be processed by GCIB processing, is held on a workpiece holder 1162, which disposes the workpiece in the path of the GCIB 1128. The workpiece holder is attached to but electrically insulated from the processing chamber 1108 by an electrical insulator 1164. Thus, GCIB 1128 striking the workpiece 1160 and the workpiece holder 1162 flows through an electrical lead 1168 to a dose processor 1170. A beam gate 1172 controls transmission of the GCIB 1128 along axis 1154 to the workpiece 1160. The beam gate 1172 typically has an open state and a closed state that is controlled by a linkage 1174 that may be (for example) electrical, mechanical, or electromechanical. Dose processor 1170 controls the open/closed state of the beam gate 1172 to manage the GCIB dose received by the workpiece 1160 and the workpiece holder 1162. In operation, the dose processor 1170 opens the beam gate 1172 to initiate GCIB irradiation of the workpiece 1160. Dose processor 1170 typically integrates GCIB electrical current arriving at the workpiece 1160 and workpiece holder 1162 to calculate an accumulated GCIB irradiation dose. At a predetermined dose, the dose processor 1170 closes the beam gate 1172, terminating processing when the predetermined dose has been achieved.

Figure 8:
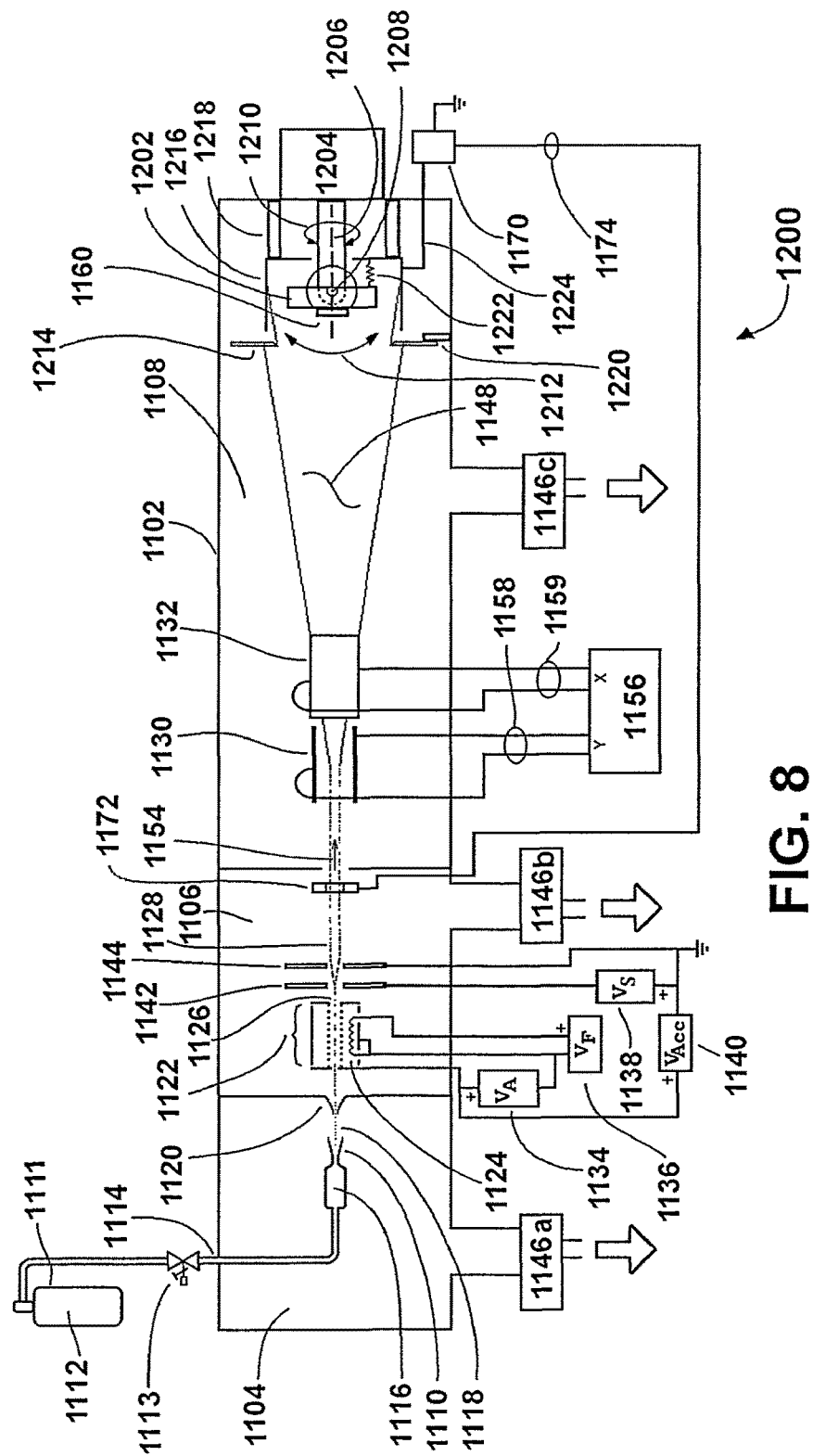
FIG. 8 is a schematic illustrating elements of another GCIB processing apparatus 1200 for workpiece processing using a GCIB, wherein scanning of the ion beam and manipulation of the workpiece is employed.

FIG. 8 shows a schematic illustrating elements of another GCIB processing apparatus 1200 for workpiece processing using a GCIB, wherein scanning of the ion beam and manipulation of the workpiece is employed. A workpiece 1160 to be processed by the GCIB processing apparatus 1200 is held on a workpiece holder 1202, disposed in the path of the GCIB 1128. In order to accomplish uniform processing of the workpiece 1160, the workpiece holder 1202 is designed to manipulate workpiece 1160, as may be required for uniform processing.

Any workpiece surfaces that are non-planar, for example, spherical or cup-like, rounded, irregular, or other un-flat configuration, may be oriented within a range of angles with respect to the beam incidence to obtain optimal GCIB processing of the workpiece surfaces. The workpiece holder 1202 can be fully articulated for orienting all non-planar surfaces to be processed in suitable alignment with the GCIB 1128 to provide processing optimization and uniformity. More specifically, when the workpiece 1160 being processed is non-planar, the workpiece holder 1202 may be rotated in a rotary motion 1210 and articulated in articulation motion 1212 by an articulation/rotation mechanism 1204. The articulation/rotation mechanism 1204 may permit 360 degrees of device rotation about longitudinal axis 1206 (which is coaxial with the axis 1154 of the GCIB 1128) and sufficient articulation about an axis 1208 perpendicular to axis 1206 to maintain the workpiece surface to within a desired range of beam incidence.

Under certain conditions, depending upon the size of the workpiece 1160, a scanning system may be desirable to produce uniform irradiation of a large workpiece. Although often not necessary for GCIB processing, two pairs of orthogonally oriented electrostatic scan plates 1130 and 1132 may be utilized to produce a raster or other scanning pattern over an extended processing area. When such beam scanning is performed, a scan generator 1156 provides X-axis scanning signal voltages to the pair of scan plates 1132 through lead pair 1159 and Y-axis scanning signal voltages to the pair of scan plates 1130 through lead pair 1158. The scanning signal voltages are commonly triangular waves of different frequencies that cause the GCIB 1128 to be converted into a scanned GCIB 1148, which scans the entire surface of the workpiece 1160. A scanned beam-defining aperture 1214 defines a scanned area. The scanned beam-defining aperture 1214 is electrically conductive and is electrically connected to the low-pressure vessel 1102 wall and supported by support member 1220. The workpiece holder 1202 is electrically connected via a flexible electrical lead 1222 to a faraday cup 1216 that surrounds the workpiece 1160 and the workpiece holder 1202 and collects all the current passing through the defining aperture 1214. The workpiece holder 1202 is electrically isolated from the articulation/rotation mechanism 1204 and the faraday cup 1216 is electrically isolated from and mounted to the low-pressure vessel 1102 by insulators 1218. Accordingly, all current from the scanned GCIB 1148, which passes through the scanned beam-defining aperture 1214 is collected in the faraday cup 1216 and flows through electrical lead 1224 to the dose processor 1170. In operation, the dose processor 1170 opens the beam gate 1172 to initiate GCIB irradiation of the workpiece 1160. The dose processor 1170 typically integrates GCIB electrical current arriving at the workpiece 1160 and workpiece holder 1202 and faraday cup 1216 to calculate an accumulated GCIB irradiation dose per unit area. At a predetermined dose, the dose processor 1170 closes the beam gate 1172, terminating processing when the predetermined dose has been achieved. During the accumulation of the predetermined dose, the workpiece 1160 may be manipulated by the articulation/rotation mechanism 1204 to ensure processing of all desired surfaces.

Figure 9:
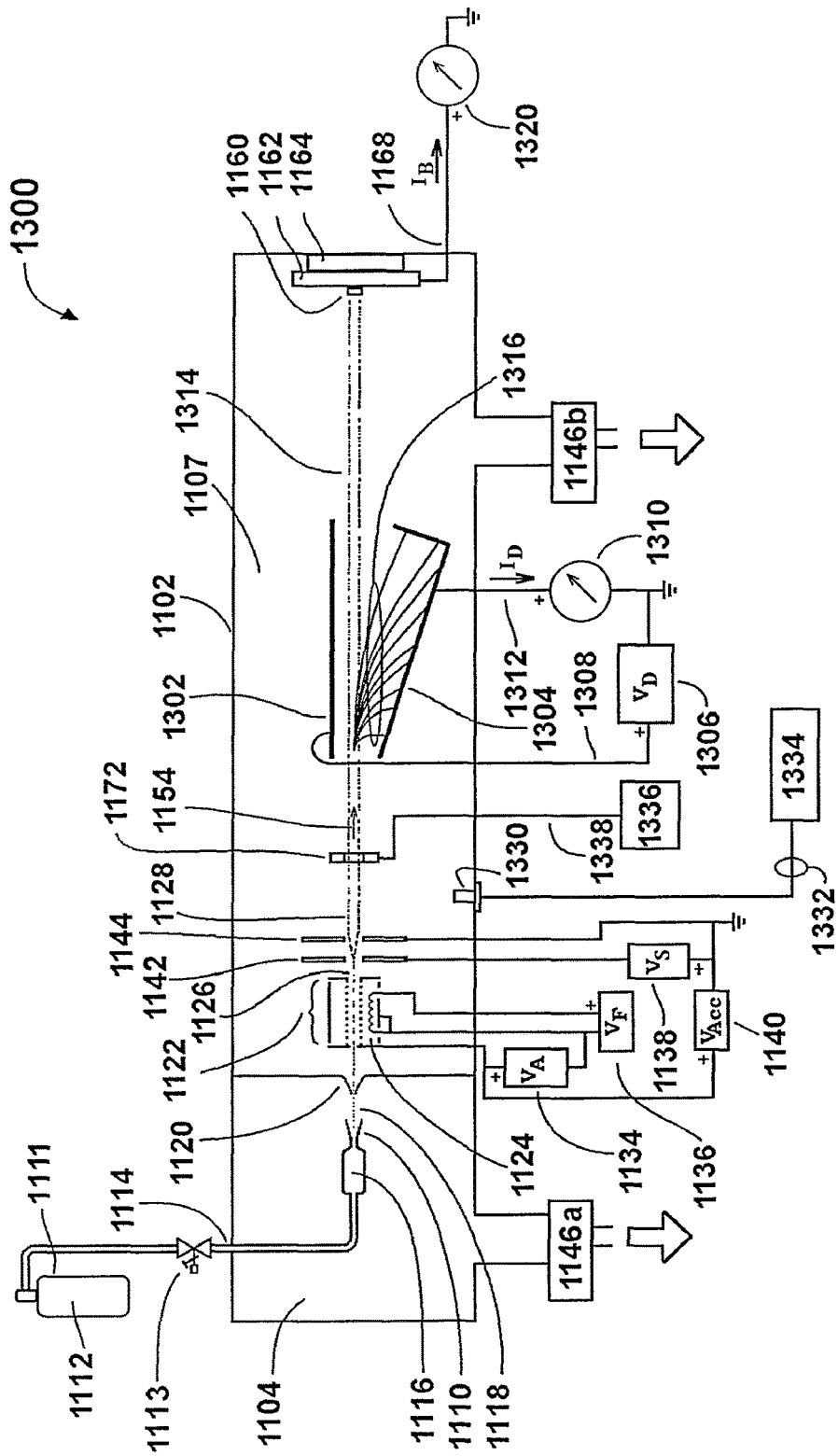
FIG. 9 is a schematic of a Neutral Beam processing apparatus 1300 according to an embodiment of the invention, which uses electrostatic deflection plates to separate the charged and uncharged beams.

FIG. 9 is a schematic of a Neutral Beam processing apparatus 1300 of an exemplary type that may be employed for Neutral Beam processing according to embodiments of the invention. It uses electrostatic deflection plates to separate the charged and uncharged portions of a GCIB. A beamline chamber 1107 encloses the ionizer and accelerator regions and the workpiece processing regions. The beamline chamber 1107 has high conductance and so the pressure is substantially uniform throughout. A vacuum pump 1146*b* evacuates the beamline chamber 1107. Gas flows into the beamline chamber 1107 in the form of clustered and unclustered gas transported by the gas jet 1118 and in the form of additional unclustered gas that leaks through the gas skimmer aperture 1120. A pressure sensor 1330 transmits pressure data from the beamline chamber 1107 through an electrical cable 1332 to a pressure sensor controller 1334, which measures and displays pressure in the beamline chamber 1107. The pressure in the beamline chamber 1107 depends on the balance of gas flow into the beamline chamber 1107 and the pumping speed of the vacuum pump 1146*b*. By selection of the diameter of the gas skimmer aperture 1120, the flow of source gas 1112 through the nozzle 1110, and the pumping speed of the vacuum pump 1146*b*, the pressure in the beamline chamber 1107 equilibrates at a pressure, PB, determined by design and by nozzle flow. The beam flight path from grounded electrode 1144 to workpiece holder 162, is for example, 100 cm. By design and adjustment PB may be approximately $6 \times 10^{-5}$ torr ($8 \times 10^{-3}$ pascal). Thus the product of pressure and beam path length is approximately $6 \times 10^{-3}$ torr-cm (0.8 pascal-cm) and the gas target thickness for the beam is approximately $1.94 \times 10^{14}$ gas molecules per cm2, which is observed to be effective for dissociating the gas cluster ions in the GCIB 1128. VAcc may be for example 30 kV and the GCIB 1128 is accelerated by that potential. A pair of deflection plates (1302 and 1304) is disposed about the axis 1154 of the GCIB 1128. A deflector power supply 1306 provides a positive deflection voltage VD to deflection plate 1302 via electrical lead 1308. Deflection plate 1304 is connected to electrical ground by electrical lead 1312 and through current sensor/display 1310. Deflector power supply 1306 is manually controllable. VD may be adjusted from zero to a voltage sufficient to completely deflect the ionized portion 1316 of the GCIB 1128 onto the deflection plate 1304 (for example a few thousand volts). When the ionized portion 1316 of the GCIB 1128 is deflected onto the deflection plate 1304, the resulting current, ID flows through electrical lead 1312 and current sensor/display 1310 for indication. When VD is zero, the GCIB 1128 is undeflected and travels to the workpiece 1160 and the workpiece holder 1162. The GCIB beam current IB is collected on the workpiece 1160 and the workpiece holder 1162 and flows through electrical lead 1168 and current sensor/display 1320 to electrical ground. IB is indicated on the current sensor/display 1320. A beam gate 1172 is controlled through a linkage 1338 by beam gate controller 1336. Beam gate controller 1336 may be manual or may be electrically or mechanically timed by a preset value to open the beam gate 1172 for a predetermined interval. In use, VD is set to zero, the beam current, IB, striking the workpiece holder is measured. Based on previous experience for a given GCIB process recipe, an initial irradiation time for a given process is determined based on the measured current, IB. VD is increased until all measured beam current is transferred from IB to ID and ID no longer increases with increasing VD. At this point a Neutral Beam 1314 comprising energetic dissociated components of the initial GCIB 1128 irradiates the workpiece holder 1162. The beam gate 1172 is then closed and the workpiece 1160 placed onto the workpiece holder 1162 by conventional workpiece loading means (not shown). The beam gate 1172 is opened for the predetermined initial radiation time. After the irradiation interval, the workpiece may be examined and the processing time adjusted as necessary to calibrate the duration of Neutral Beam processing based on the measured GCIB beam current IB. Following such a calibration process, additional workpieces may be processed using the calibrated exposure duration.

The Neutral Beam 1314 contains a repeatable fraction of the initial energy of the accelerated GCIB 1128. The remaining ionized portion 1316 of the original GCIB 1128 has been removed from the Neutral Beam 1314 and is collected by the grounded deflection plate 1304. The ionized portion 1316 that is removed from the Neutral Beam 1314 may include monomer ions and gas cluster ions including intermediate size gas cluster ions. Because of the monomer evaporation mechanisms due to cluster heating during the ionization process, intra-beam collisions, background gas collisions, and other causes (all of which result in erosion of clusters) the Neutral Beam substantially consists of neutral monomers, while the separated charged particles are predominately cluster ions. The inventors have confirmed this by suitable measurements that include re-ionizing the Neutral Beam and measuring the charge to mass ratio of the resulting ions. As will be shown below, certain superior process results are obtained by processing workpieces using this Neutral Beam.

Figure 10:
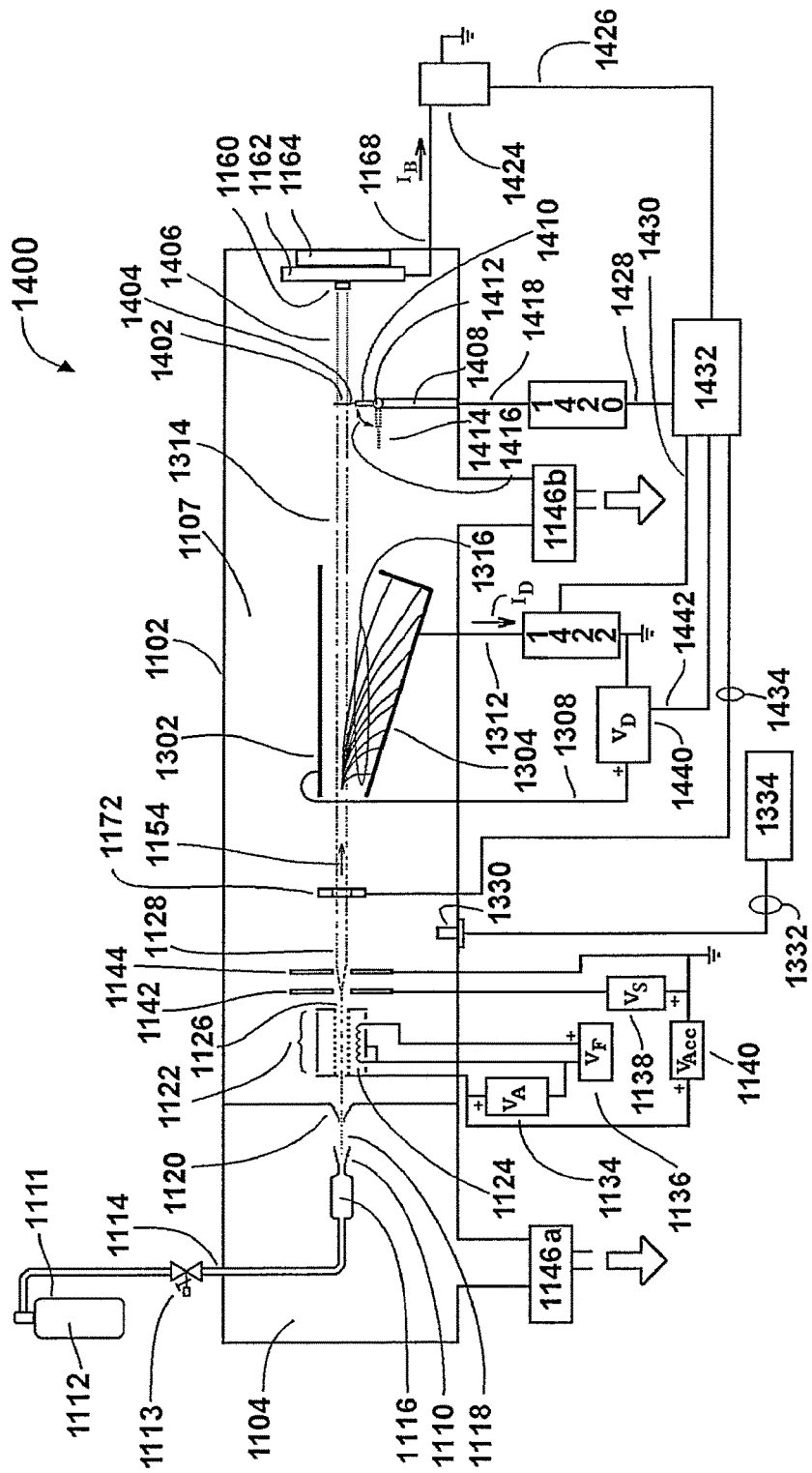
FIG. 10 is a schematic of a Neutral Beam processing apparatus 1400 according to an embodiment of the invention, using a thermal sensor for Neutral Beam measurement.

FIG. 10 is a schematic of a Neutral Beam processing apparatus 1400 as may, for example, be used in generating Neutral Beams as may be employed in embodiments of the invention. It uses a thermal sensor for Neutral Beam measurement. A thermal sensor 1402 attaches via low thermal conductivity attachment 1404 to a rotating support arm 1410 attached to a pivot 1412. Actuator 1408 moves thermal sensor 1402 via a reversible rotary motion 1416 between positions that intercept the Neutral Beam 1314 or GCIB 1128 and a parked position indicated by 1414 where the thermal sensor 1402 does not intercept any beam. When thermal sensor 1402 is in the parked position (indicated by 1414) the GCIB 1128 or Neutral Beam 1314 continues along path 1406 for irradiation of the workpiece 1160 and/or workpiece holder 1162. A thermal sensor controller 1420 controls positioning of the thermal sensor 1402 and performs processing of the signal generated by thermal sensor 1402. Thermal sensor 1402 communicates with the thermal sensor controller 1420 through an electrical cable 1418. Thermal sensor controller 1420 communicates with a dosimetry controller 1432 through an electrical cable 1428. A beam current measurement device 1424 measures beam current IB flowing in electrical lead 1168 when the GCIB 1128 strikes the workpiece 1160 and/or the workpiece holder 1162. Beam current measurement device 1424 communicates a beam current measurement signal to dosimetry controller 1432 via electrical cable 1426. Dosimetry controller 1432 controls setting of open and closed states for beam gate 1172 by control signals transmitted via linkage 1434. Dosimetry controller 1432 controls deflector power supply 1440 via electrical cable 1442 and can control the deflection voltage VD between voltages of zero and a positive voltage adequate to completely deflect the ionized portion 1316 of the GCIB 1128 to the deflection plate 1304. When the ionized portion 1316 of the GCIB 1128 strikes deflection plate 1304, the resulting current ID is measured by current sensor 1422 and communicated to the dosimetry controller 1432 via electrical cable 1430. In operation dosimetry controller 1432 sets the thermal sensor 1402 to the parked position 1414, opens beam gate 1172, sets VD to zero so that the full GCIB 1128 strikes the workpiece holder 1162 and/or workpiece 1160. The dosimetry controller 1432 records the beam current IB transmitted from beam current measurement device 1424. The dosimetry controller 1432 then moves the thermal sensor 1402 from the parked position 1414 to intercept the GCIB 1128 by commands relayed through thermal sensor controller 1420. Thermal sensor controller 1420 measures the beam energy flux of GCIB 1128 by calculation based on the heat capacity of the sensor and measured rate of temperature rise of the thermal sensor 1402 as its temperature rises through a predetermined measurement temperature (for example 70 degrees C.) and communicates the calculated beam energy flux to the dosimetry controller 1432 which then calculates a calibration of the beam energy flux as measured by the thermal sensor 1402 and the corresponding beam current measured by the beam current measurement device 1424. The dosimetry controller 1432 then parks the thermal sensor 1402 at parked position 1414, allowing it to cool and commands application of positive VD to deflection plate 1302 until all of the current ID due to the ionized portion of the GCIB 1128 is transferred to the deflection plate 1304. The current sensor 1422 measures the corresponding ID and communicates it to the dosimetry controller 1432. The dosimetry controller also moves the thermal sensor 1402 from parked position 1414 to intercept the Neutral Beam 1314 by commands relayed through thermal sensor controller 420. Thermal sensor controller 420 measures the beam energy flux of the Neutral Beam 1314 using the previously determined calibration factor and the rate of temperature rise of the thermal sensor 1402 as its temperature rises through the predetermined measurement temperature and communicates the Neutral Beam energy flux to the dosimetry controller 1432. The dosimetry controller 1432 calculates a neutral beam fraction, which is the ratio of the thermal measurement of the Neutral Beam 1314 energy flux to the thermal measurement of the full GCIB 1128 energy flux at sensor 1402. Under typical operation, a neutral beam fraction of from about 5% to about 95% is achieved. Before beginning processing, the dosimetry controller 1432 also measures the current, ID, and determines a current ratio between the initial values of IB and ID. During processing, the instantaneous ID measurement multiplied by the initial IB/ID ratio may be used as a proxy for continuous measurement of the IB and employed for dosimetry during control of processing by the dosimetry controller 1432. Thus the dosimetry controller 1432 can compensate any beam fluctuation during workpiece processing, just as if an actual beam current measurement for the full GCIB 1128 were available. The dosimetry controller uses the neutral beam fraction to compute a desired processing time for a particular beam process. During the process, the processing time can be adjusted based on the calibrated measurement of ID for correction of any beam fluctuation during the process.

Figure 3:
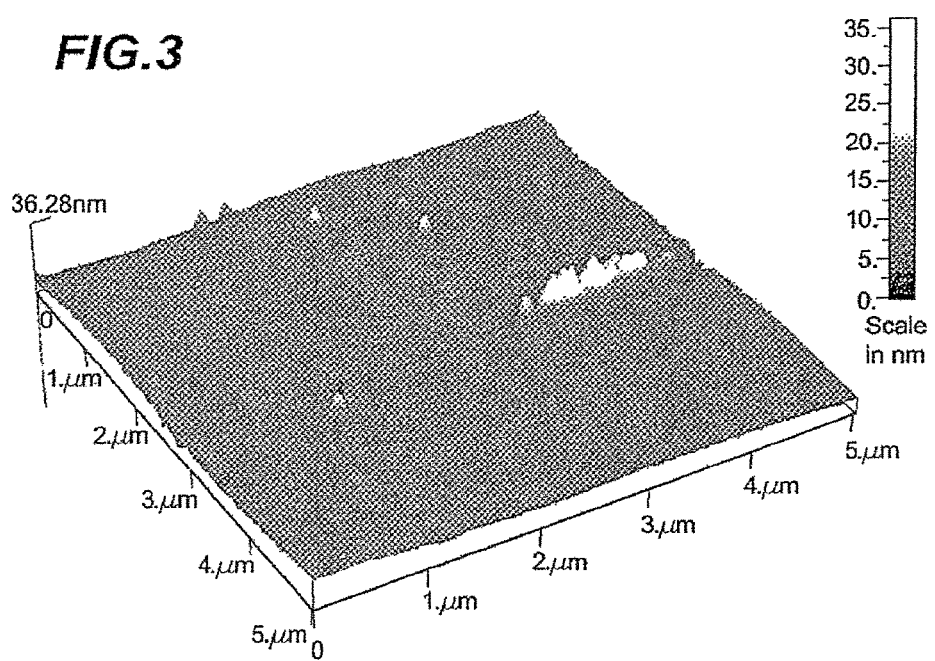
FIG. 3 is an atomic force microscope image showing the surface of a coronary stent before GCIB processing.
Figure 4:
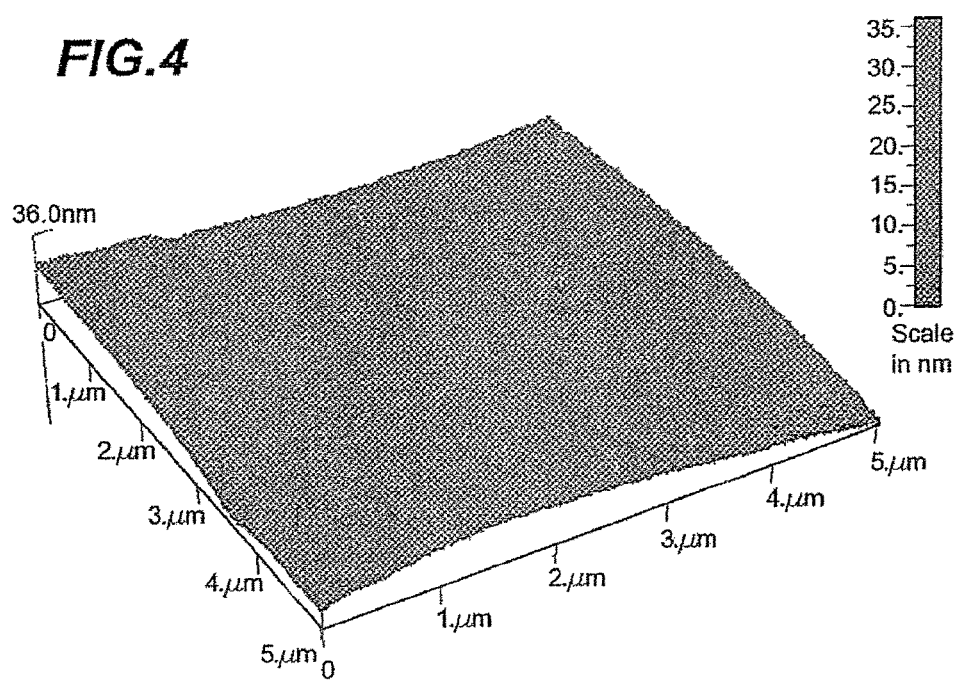
FIG. 4 is an atomic force microscope image showing the surface of a coronary stent after GCIB processing.

As the atomic force microscope (AFM) images shown in FIGS. 3 and 4 demonstrate, it is possible to dramatically affect the medical device surface utilizing gas cluster ion beam processing. FIG. 3 shows a stent surface before GCIB treatment with gross surface micro-roughness on a strut edge. The surface roughness measured an Ra of 113 angstroms and an RRMS of 148 angstroms. These irregularities highlight the surface condition at the cellular level where thrombosis begins. FIG. 4 shows the stent surface after GCIB processing where the surface micro-roughness has been eliminated without any measurable physical or structural change to the integrity of the stent itself. The post-GCIB surface roughness measured an Ra of 19 angstroms and an RRMS of 25 angstroms. In this manner, GCIB processing also provides the added benefit of smoothing the surface of the medical device. Non-smooth surfaces may snare fibrinogen, platelets, and other matter further promoting stenosis.

Figure 5:
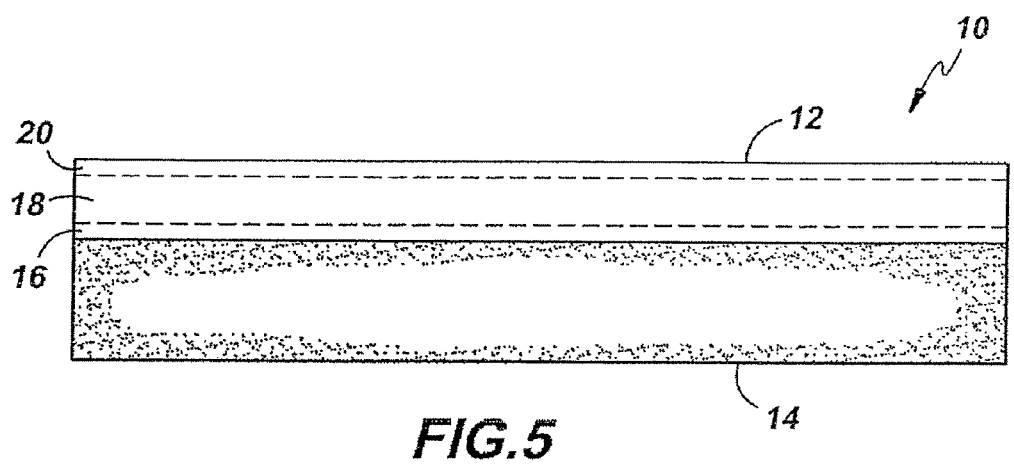
FIG. 5 is a cross section of a drug delivery system prior to processing in accordance with the present invention.

With reference to FIG. 5, a drug delivery system 10, which includes a drug-containing medium 12 and an optional substrate or medical device 14, is shown prior to processing by the method of the present invention. Medical device 14 is only representational and may take any suitable form. Device 14 may include an implantable medical device such as a stent or any other medical device, which may benefit from an in situ drug delivery mechanism. Optionally, the use of substrate or device 14 may be limited to the fabrication of drug containing medium 12, wherein substrate or device 14 is removed from medium 12 prior to implantation. Substrate or device 14 maybe he constructed of any suitable material such as, for example, metal, ceramic or a polymer. Portions of substrate or device 14 may also be surface treated using GCIB in accordance with the method mentioned above, prior to the application of drug/polymer medium 12.

Drug containing medium 12 may take any suitable form such as the various polymer arrangements discussed above. Medium 12 may include just a single layer of drug containing material, or it may include multiple layers 16, 18, 20, as described above. Although the existing art identifies the use of an outer layer to control initial drug release, the process of the present invention may be used with this known arrangement to further control surface characteristics of the medium, including the drug release rate after initial in situ liquid exposure. Drug medium 12 may be applied to device 14 in any suitable arrangement from just a portion to complete or almost complete enclosure of device 14.

One method of application of medium 12 to device 14 uses a drug polymer mixture with a volatile solvent, which is deposited upon a surface of device 14. The solvent is evaporated to leave a cohesive drug/polymer mixture in the form of medium 12, attached to the substrate. Once the solvent is evaporated, drug medium 12 may form a cohesive mixture or mass and thereby provide a suitable drug delivery system, even in the absence of device 14.

Figure 6:
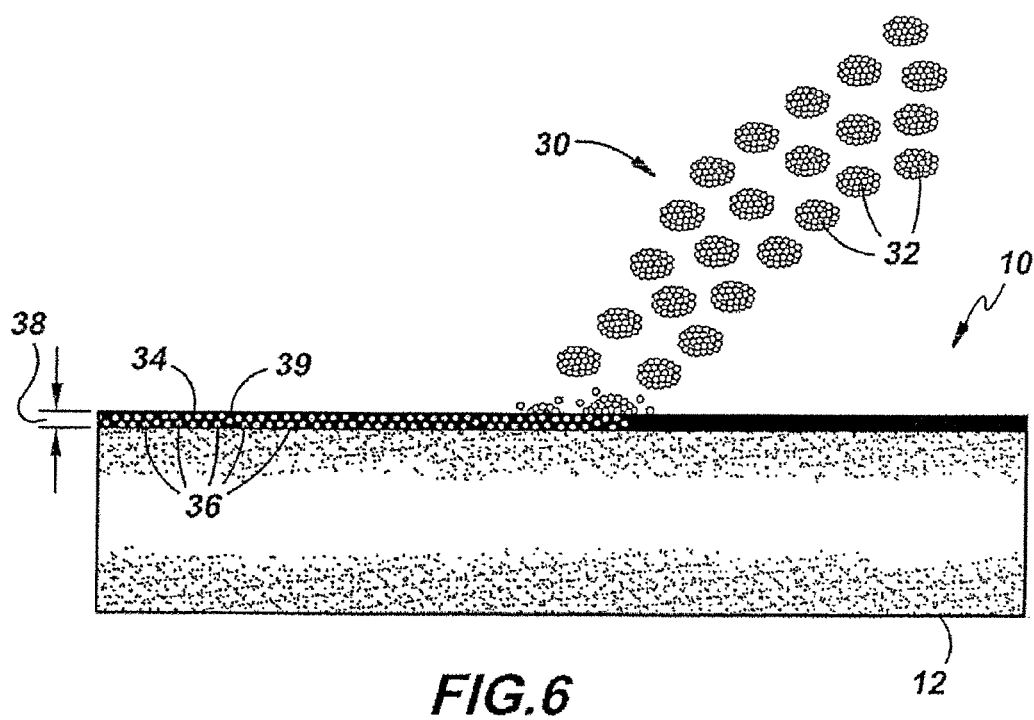
FIG. 6 is a cross section of the drug delivery system of FIG. 5 shown during gas cluster ion beam processing performed in accordance with the present invention.

With reference to FIG. 6, the drug delivery system 10 is shown undergoing irradiation with a gas cluster ion beam. A stream 30 of gas cluster molecules is being scanned across the cross section of drug delivery device 10. The clusters 32 break up upon impact with the surface 34 resulting in the shallow implantation of individual or small groups of molecules 36. Most of the individual molecules 36 stop within the first couple of molecular levels of medium 12 with the result that most of a thin layer 38 at surface 34 is densified or carbonized by the impinging molecules. The sealing of surface 34 is not complete, as various openings 39 remain in surface 34 which openings allow for the elution of drugs from medium 12. Thus, it is through the amount of GCIB irradiation that the characteristics of surface 34 are determined. The greater the amount of irradiation, the fewer and smaller are the openings in surface 34, thereby slowing the release of drugs from medium 12. Also, this densification or carbonization of surface 34 causes pacification or sealing of surface 34, which can decrease the bio-reactivity of surface 34 in contact with living tissue. In the case of some polymer materials which may be used for medium 12, the densification or carbonization can limit the release of volatile organic compounds by the medium 12 into surrounding living tissue. Thus, the process of the present invention enhances the choices of materials which may be used to construct medium 12 and can reduce risk factors associated with those material choices.

FIGS. 11A through 11D show the comparative effects of full and charge separated beams on a gold thin film. In an experimental setup, a gold film deposited on a silicon substrate was processed by a full GCIB (charged and neutral components), a Neutral Beam (charged components deflected out of the beam), and a deflected beam comprising only charged components. All three conditions are derived from the same initial GCIB, a 30 kV accelerated Ar GCIB. Gas target thickness for the beam path after acceleration was approximately $2\times10^{14}$ argon gas atoms per cm2. For each of the three beams, exposures were matched to the total energy carried by the full beam (charged plus neutral) at an ion dose of $2\times10^{15}$ gas cluster ions per cm2. Energy flux rates of each beam were measured using a thermal sensor and process durations were adjusted to ensure that each sample received the same total thermal energy dose equivalent to that of the full (charged plus neutral) GCIB dose.

Figure 11A:
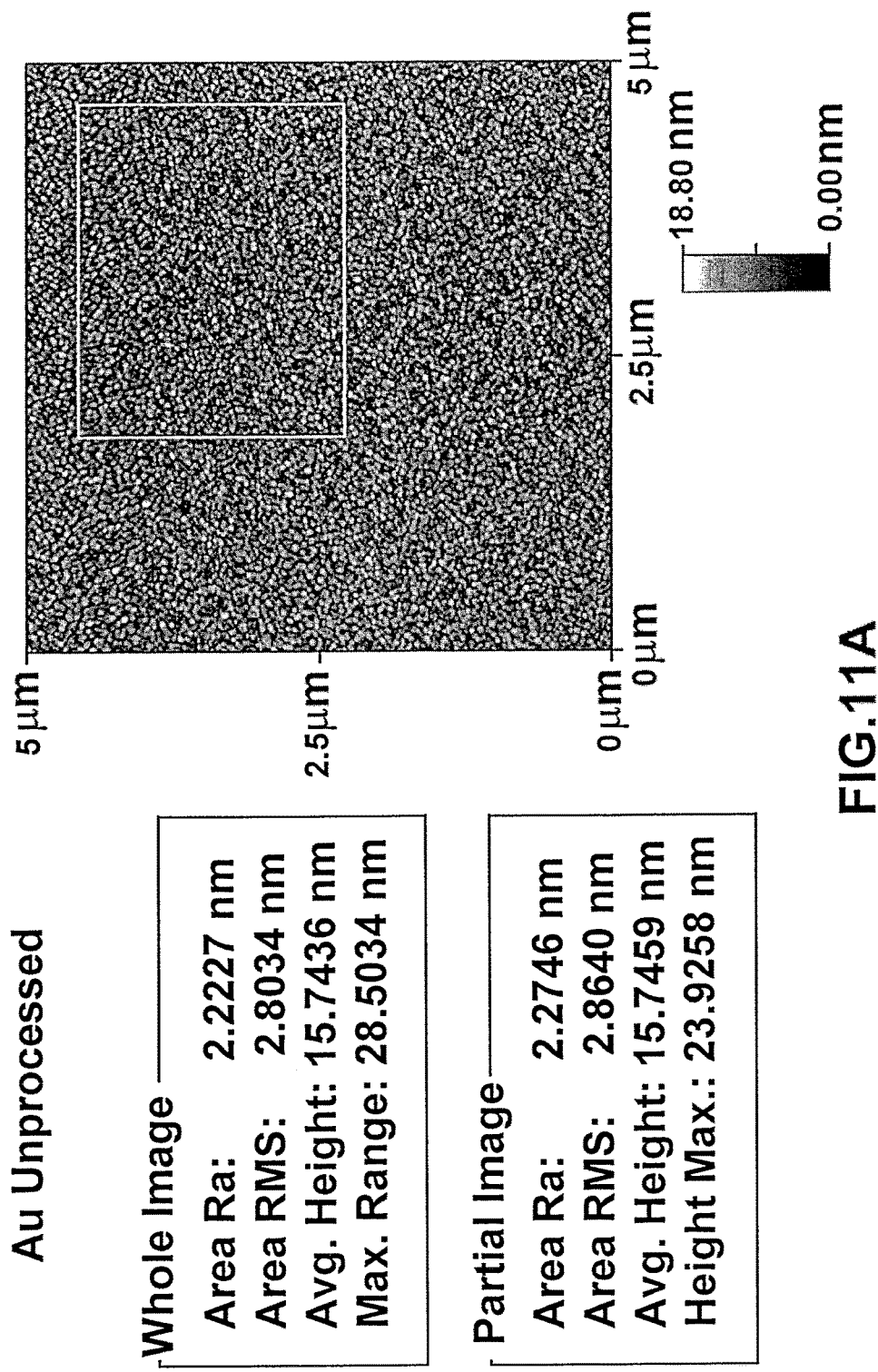
FIGS. 11A, 11B, 11C, and 11D show processing results indicating that for a metal surface, processing by a neutral component of a beam produces superior smoothing of the film compared to processing with either a full GCIB or a charged component of the beam.
Figure 11B:
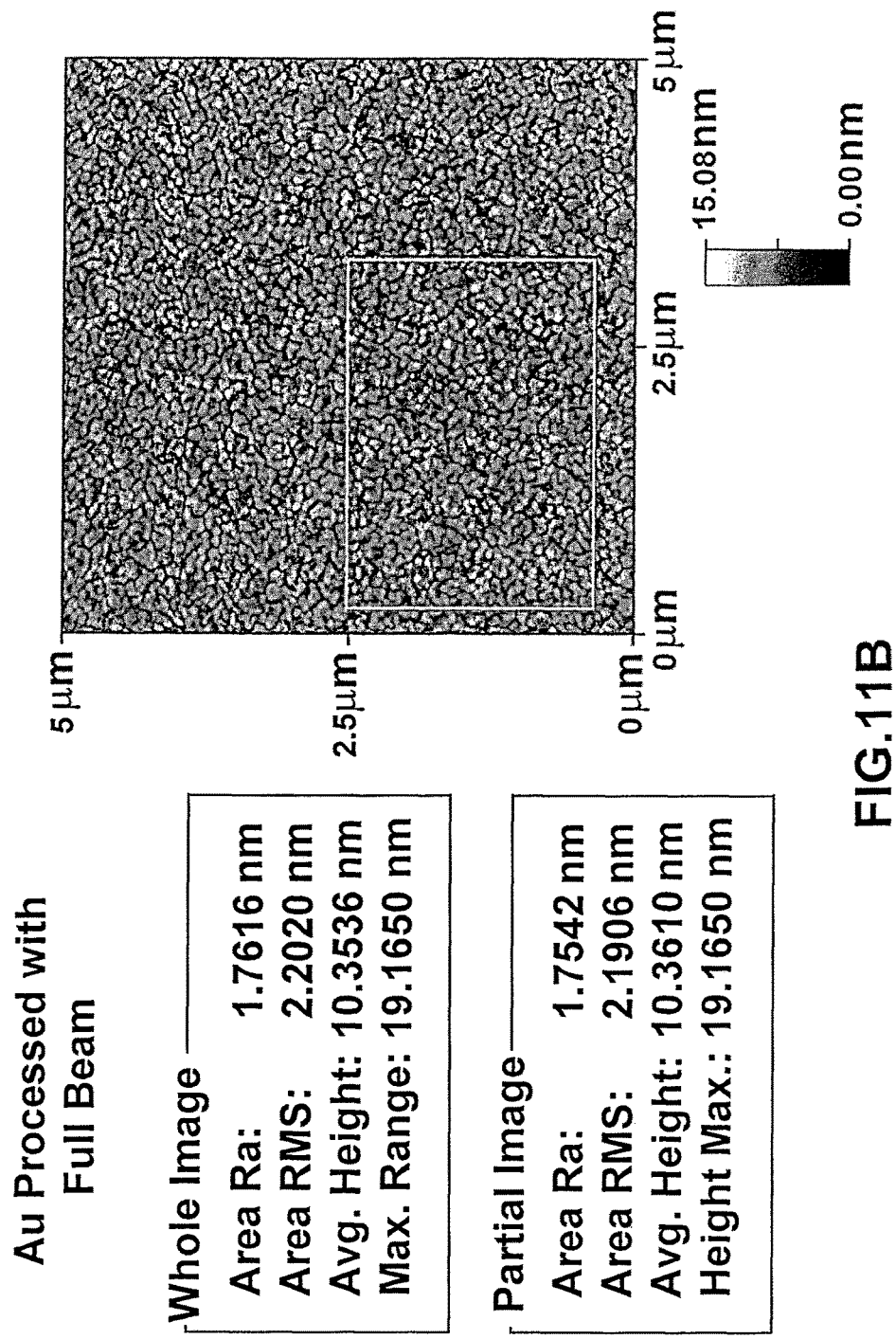
Figure 11C:
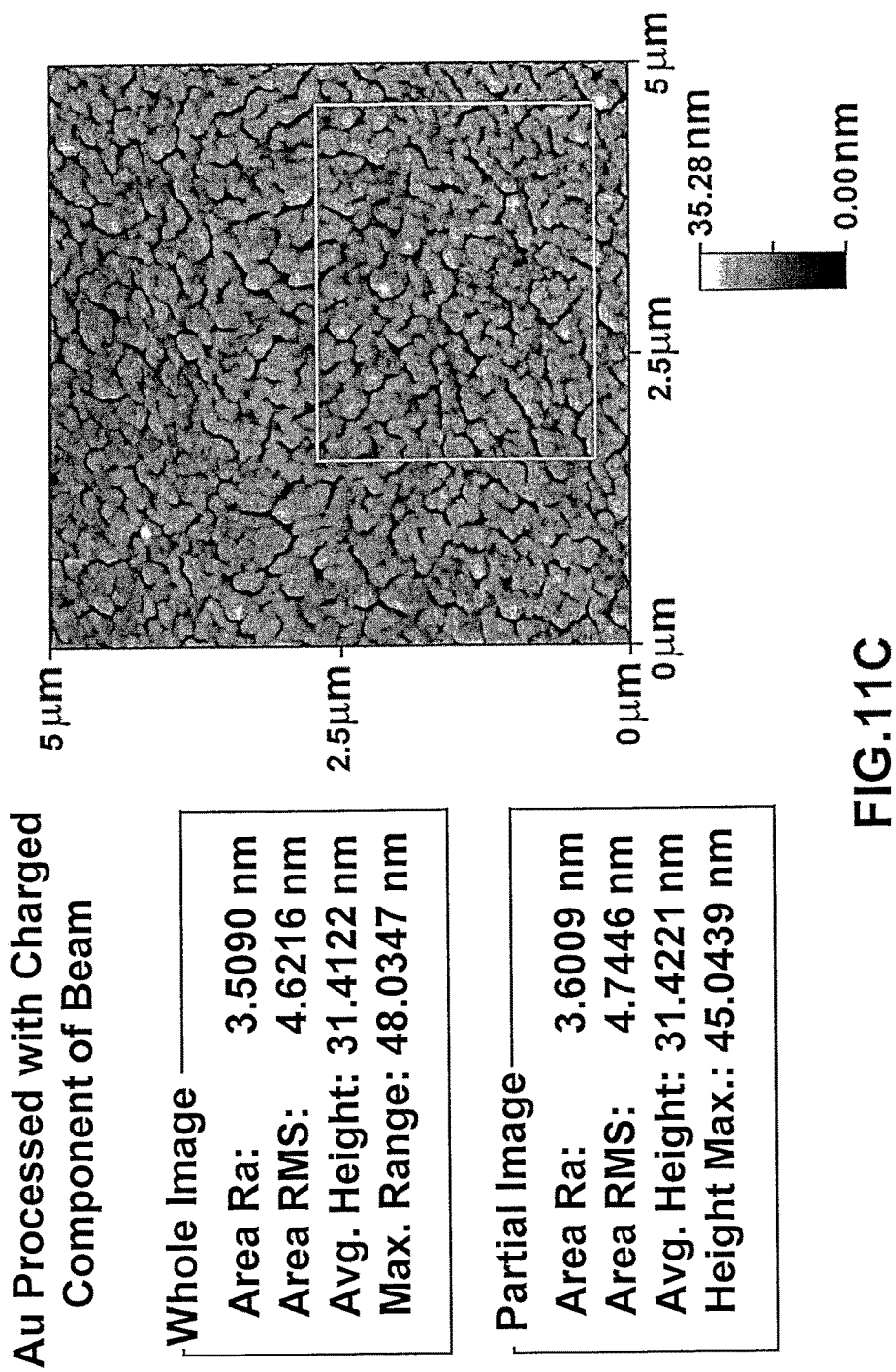
Figure 11D:
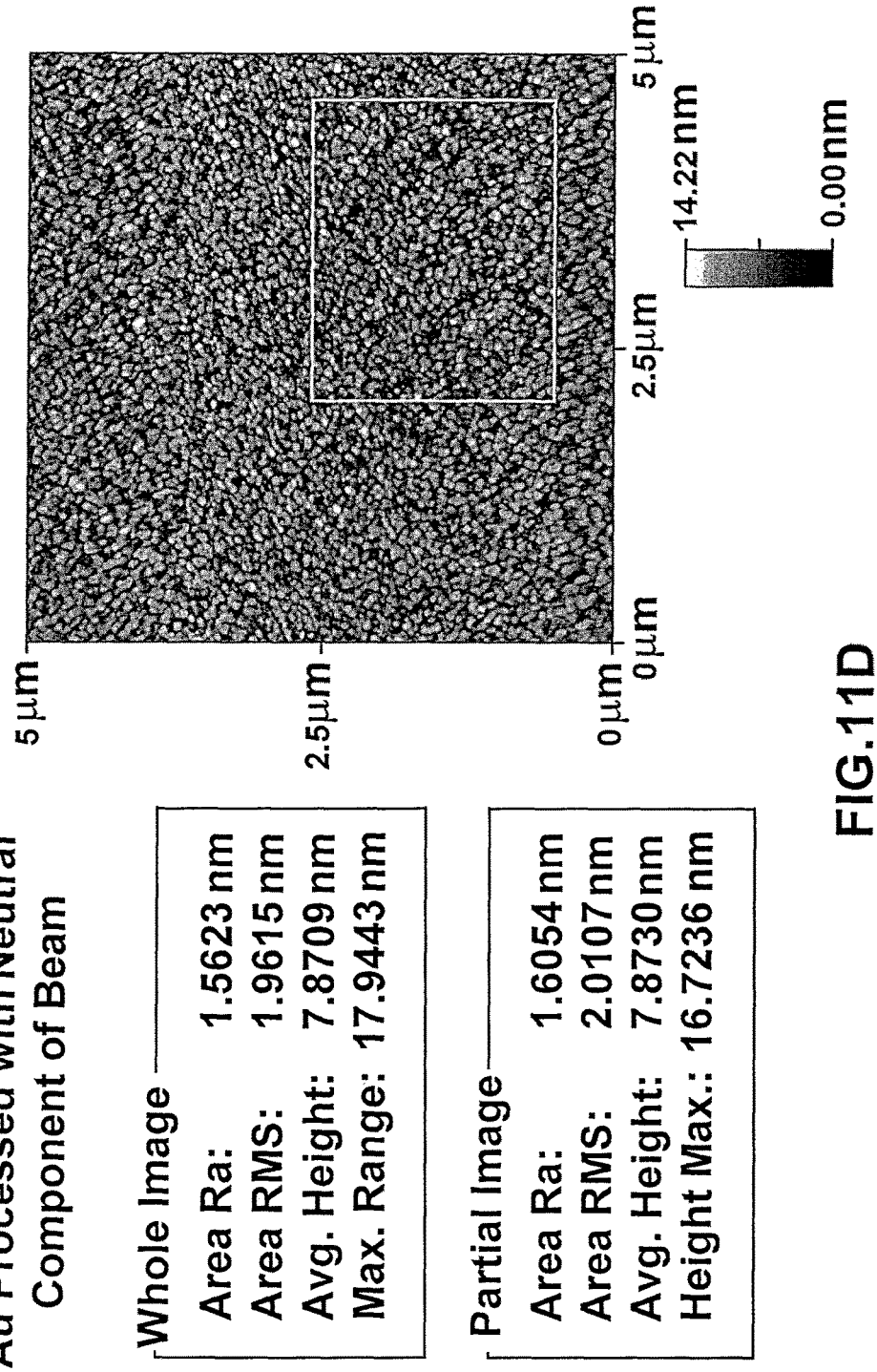

FIG. 11A shows an atomic force microscope (AFM) 5 micron by 5 micron scan and statistical analysis of an as-deposited gold film sample that had an average roughness, Ra, of approximately 2.22 nm. FIG. 11B shows an AFM scan of the gold surface processed with the full GCIB—average roughness, Ra, has been reduced to approximately 1.76 nm. FIG. 11C shows an AFM scan of the surface processed using only charged components of the beam (after deflection from the neutral beam components)—average roughness, Ra, has been increased to approximately 3.51 nm. FIG. 11D shows an AFM scan of the surface processed using only the neutral component of the beam (after charged components were deflected out of the Neutral Beam)—average roughness, Ra, is smoothed to approximately 1.56 nm. The full GCIB processed sample (B) is smoother than the as deposited film (A). The Neutral Beam processed sample (D) is smoother than the full GCIB processed sample (B). The sample (C) processed with the charged component of the beam is substantially rougher than the as-deposited film. The results support the conclusion that the neutral portions of the beam contribute to smoothing and the charged components of the beam contribute to roughening. Thus it is seen that accelerated Neutral Beams derived from a GCIB provide superior smoothing even to that of GCIB.

Figure 12A:
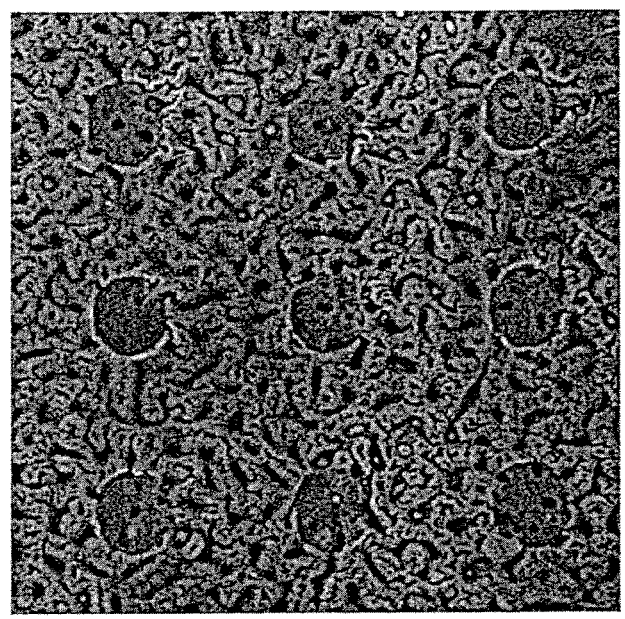
FIGS. 12A and 12B show comparison of a drug coating on a cobalt-chrome coupon representing a drug eluting medical device, wherein processing with a Neutral Beam produces a superior result to processing with a full GCIB.
Figure 12B:
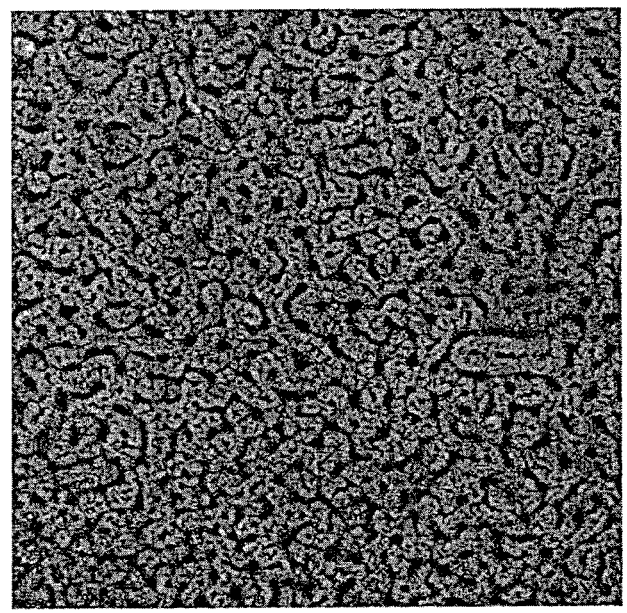

FIGS. 12A and 12B show comparative results of full GCIB and Neutral Beam processing of a drug film deposited on a cobalt-chrome coupon used to evaluate drug elution rate for a drug eluting coronary stent. FIG. 12A represents a sample irradiated using an argon GCIB (including the charged and neutral components) accelerated using VAcc of 30 kV with an irradiated dose of $2\times10^{15}$ gas cluster ions per cm2. FIG. 12B represents a sample irradiated using a Neutral Beam derived from an argon GCIB accelerated using VAcc of 30 kV. The Neutral Beam was irradiated with a thermal energy dose equivalent to that of a 30 kV accelerated, $2\times10^{15}$ gas cluster ion per cm2 dose (equivalent determined by beam thermal energy flux sensor). The irradiation for both samples was performed through a cobalt chrome proximity mask having an array of circular apertures of approximately 50 microns diameter for allowing beam transmission. FIG. 12A is a scanning electron micrograph of a 300 micron by 300 micron region of the sample that was irradiated through the mask with full beam. FIG. 12B is a scanning electron micrograph of a 300 micron by 300 micron region of the sample that was irradiated through the mask with a Neutral Beam. The sample shown in FIG. 12A exhibits damage and etching caused by the full beam where it passed through the mask. The sample shown in FIG. 12B exhibits no visible effect. In elution rate tests in physiological saline solution, the samples processed like the Figure B sample (but without mask) exhibited superior (delayed) elution rate compared to the samples processed like the FIG. 12A sample (but without mask). The results support the conclusion that processing with the Neutral Beam contributes to the desired delayed elution effect, while processing with the full GCIB (charged plus neutral components) contributes to weight loss of the drug by etching, with inferior (less delayed) elution rate effect.

To further illustrate the ability of an accelerated Neutral Beam derived from an accelerated GCIB to aid in attachment of a drug to a surface and to provide drug modification in such a way that it results in delayed drug elution, an additional test was performed. Silicon coupons approximately 1 cm by 1 cm (1 cm2) were prepared from highly polished clean semiconductor-quality silicon wafers for use as drug deposition substrates. A solution of the drug Rapamycin (Catalog number R-5000, LC Laboratories, Woburn, Mass. 01801, USA) was formed by dissolving 500 mg of Rapamycin in 20 ml of acetone. A pipette was then used to dispense approximately 5 micro-liter droplets of the drug solution onto each coupon. Following atmospheric evaporation and vacuum drying of the solution, this left approximately 5 mm diameter circular Rapamycin deposits on each of the silicon coupons. Coupons were divided into groups and either left un-irradiated (controls) or irradiated with various conditions of Neutral Beam irradiation. The groups were then placed in individual baths (bath per coupon) of human plasma for 4.5 hours to allow elution of the drug into the plasma. After 4.5 hours, the coupons were removed from the plasma baths, rinsed in deionized water and vacuum dried. Weight measurements were made at the following stages in the process: 1) pre-deposition clean silicon coupon weight; 2) following deposition and drying, weight of coupon plus deposited drug; 3) post-irradiation weight; and 4) post plasma-elution and vacuum drying weight. Thus for each coupon the following information is available: 1) initial weight of the deposited drug load on each coupon; 2) the weight of drug lost during irradiation of each coupon; and 3) the weight of drug lost during plasma elution for each coupon. For each irradiated coupon it was confirmed that drug loss during irradiation was negligible. Drug loss during elution in human plasma is shown in Table 1. The groups were as follows: Control Group—no irradiation was performed; Group 1—irradiated with a Neutral Beam derived from a GCIB accelerated with a VAcc of 30 kV. The Group 1 irradiated beam energy dose was equivalent to that of a 30 kV accelerated, $5 \times 10^{14}$ gas cluster ion per cm2 dose (energy equivalence determined by beam thermal energy flux sensor); Group 2—irradiated with a Neutral Beam derived from a GCIB accelerated with a VAcc of 30 kV. The Group 2 irradiated beam energy dose was equivalent to that of a 30 kV accelerated, $1 \times 10^{14}$ gas cluster ion per cm2 dose (energy equivalence determined by beam thermal energy flux sensor); and Group 3—irradiated with a Neutral Beam derived from a GCIB accelerated with a VAcc of 25 kV. The Group 3 irradiated beam energy dose was equivalent to that of a 25 kV accelerated, $5 \times 10^{14}$ gas cluster ion per cm2 dose (energy equivalence determined by beam thermal energy flux sensor).

Table 1 shows that for every case of Neutral Beam irradiation (Groups 1 through 3), the drug lost during a 4.5-hour elution into human plasma was much lower than for the un-irradiated Control Group. This indicates that the Neutral Beam irradiation results in better drug adhesion and/or reduced elution rate as compared to the un-irradiated drug. The p values (heterogeneous unpaired T-test) indicate that for each of the Neutral Beam irradiated Groups 1 through 3, relative to the Control Group, the difference in the drug retention following elution in human plasma was statistically significant.

Figure 13A:
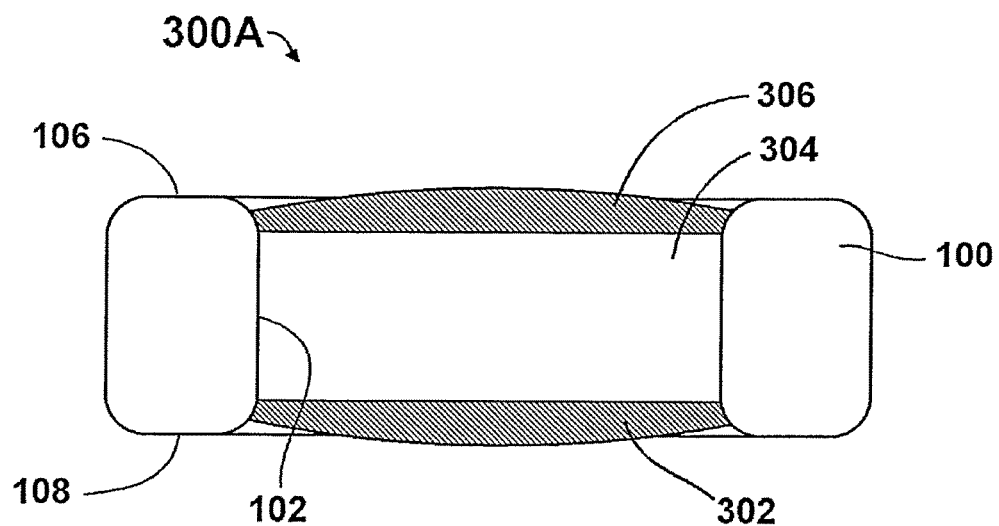
FIGS. 13A, 13B, and 13C are views of prior art holes in prior art stents, illustrating various prior art loading of holes by employing polymers.

FIG. 13A shows a sectional view 300A of a prior art hole 102 in prior art stent 100, illustrating a prior art method of loading a hole with a drug by employing polymers. A therapeutic layer 304 consists of a drug or a drug-polymer mixture. A barrier layer 302 on the inner surface 108 of the stent 100 comprises a polymer and prevents elution or controls the elution rate of the therapeutic layer 304 to the inner portion (lumen) of the stent. A second barrier layer 306 on the outer surface 106 of the stent 100 comprises a polymer and controls the elution rate of the therapeutic layer 304 to the outer portion (vascular scaffold) of the stent. The barrier layers 302 and 306 may also control or prevent the diffusion of water or other biological fluids from outside of the stent into the therapeutic layer 304 retained by the hole in the stent. The barrier layers 302 and 306 may be biodegradable or erodible materials comprising polymer to provide a delayed release of the enclosed therapeutic layer 304. The therapeutic layer 304 may be a drug or alternatively may be a mixture of drug and polymer to further delay or control the elution or release rate of the therapeutic layer 304.

Figure 13B:
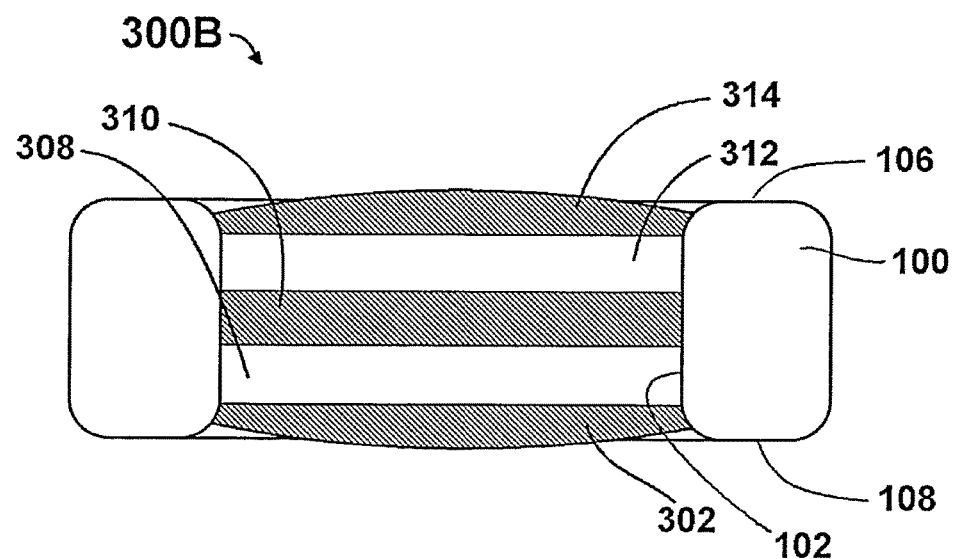

FIG. 13B shows a sectional view 300B of a prior art hole 102 in prior art stent 100, illustrating a prior art method of loading a hole with multiple layers of a drug by employing polymers. Therapeutic layers 308, 312 consist respectively of a drug or a drug-polymer mixture and may comprise similar or dissimilar drugs. Barrier layer 302 on the inner surface 108 of the stent 100 comprises a polymer and prevents elution or controls the elution rate of the therapeutic layer 308 to the inner portion (lumen) of the stent. A second barrier layer 314 on the outer surface 106 of the stent 100 comprises a polymer and controls the elution rate of the therapeutic layer 312 to the outer portion (vascular scaffold) of the stent. A third barrier layer 310 may comprise polymer

TABLE 1

| | | | | Group | | | | | | | |
|---|---|---|---|---|---|---|---|---|---|---|---|
| | | | | | | Group 1 | | Group 2 [Dose] | | Group 3 | |
| | | | | | | $[5 \times 10^{14}]$ | | $[1 \times 10^{14}]$ $\{V_{Acc}\}$ | | $[5 \times 10^{14}]$ | |
| | | Control | | | {30 kV} | | | {30 kV} | | {25 kV} | |
| Coupon # | Start Load (µg) | Elution Loss (µg) | Elution Loss % | Start Load (µg) | Elution Loss (µg) | Elution Loss % | Start Load (µg) | Elution Loss (µg) | Loss % | Start Load (µg) | Elution Loss (µg) | Elution Loss % |
| 1 | 83 | 60 | 72 | 88 | 4 | 5 | 93 | 10 | 11 | 88 | — | 0 |
| 2 | 87 | 55 | 63 | 100 | 7 | 7 | 102 | 16 | 16 | 82 | 5 | 6 |
| 3 | 88 | 61 | 69 | 83 | 2 | 2 | 81 | 35 | 43 | 93 | 1 | 1 |
| 4 | 96 | 72 | 75 | — | — | — | 93 | 7 | 8 | 84 | 3 | 4 |
| Mean | 89 | 62 | 70 | 90 | 4 | 5 | 92 | 17 | 19 | 87 | 2 | 3 |
| σ | 5 | 7 | | 9 | 3 | | 9 | 13 | | 5 | 2 | |
| p value | | | | | 0.00048 | | | 0.014 | | | 0.00003 | | and separates the therapeutic layers 308 and 312 and may also prevent the elution or control the elution rate of the therapeutic layers 308 and 310. The barrier layers 302, 310 and 314 may also control or prevent the diffusion of water or other biological fluids from outside of the stent into the therapeutic layers 308 and 312 retained by the hole in the stent. The barrier layers 302, 310, and 314 may be biodegradable or erodible materials comprising polymer to provide a delayed release of the enclosed therapeutic layers 308 and 312. The therapeutic layers 308 and 312 may be each be either a drug or alternatively may be a mixture of drug and polymer to further delay or control the elution or release rate of the therapeutic layers 308 and 312.

Figure 13C:
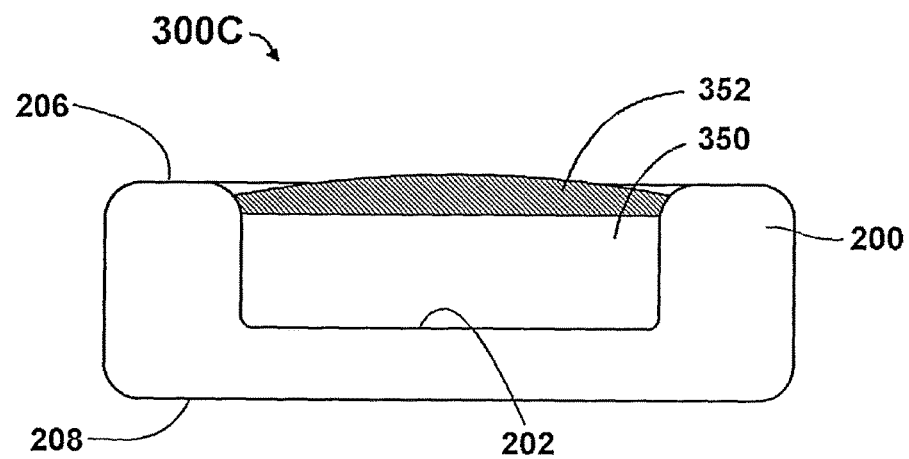

FIG. 13C shows a sectional view 300C of a prior art blind-hole 202 in a prior art stent 200, illustrating a prior art method of loading a hole with a drug by employing polymers. A therapeutic layer 350 consists of a drug or a drug-polymer mixture. A barrier layer 352 on the outer surface 206 of the stent 200 comprises a polymer and controls the elution rate of the therapeutic layer 350 to the outer portion (vascular scaffold) of the stent. The barrier layer 352 may also control or prevent the diffusion of water or other biological fluids from outside of the stent into the therapeutic layer 350 retained by the hole in the stent. The barrier layer 352 may be biodegradable or erodible material comprising polymer to provide a delayed release of the enclosed therapeutic layer 350. The therapeutic layer 350 may be a drug or alternatively may be a mixture of drug and polymer to further delay or control the elution or release rate of the therapeutic material.

Figure 14A:
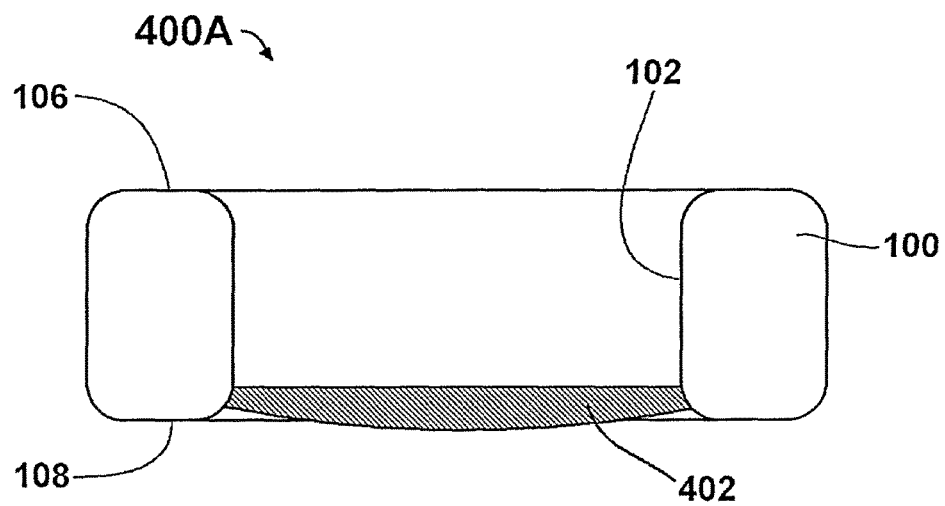
FIGS. 14A, 14B, 14C, and 14D show steps in the formation of a drug loaded through-hole in a stent according to an embodiment of the invention.

FIG. 14A shows sectional view 400A of a strut of a stent illustrating a step in the formation of a drug-loaded through-hole in a stent 100 according to an embodiment of the invention. A stent 100 has a through-hole 102. The stent has an inner surface 108 forming the lumen of the stent and has an outer surface 106 forming the vascular scaffold portion of the stent. As a step in the embodiment of the invention, a barrier layer 402 is deposited on the inner surface 108 of the stent 100 according to known technology. The barrier layer 402 may consist of polymer or of other biocompatible barrier material.

Figure 14B:
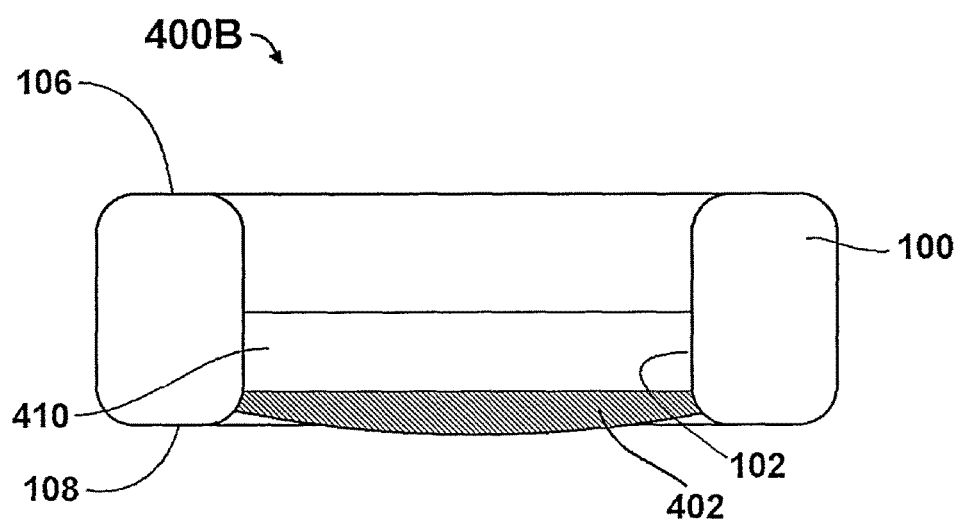

FIG. 14B shows sectional view 400B of a strut of a stent illustrating a step in the formation of a drug-loaded through-hole in a stent 100 following the step shown in FIG. 14A. In the step shown in FIG. 14B, a drug 410 is deposited in the hole 102 in the stent 100. The deposition of the drug 410 may be by any of numerous methods, including spraying, dipping, electrostatic deposition, ultrasonic spraying, vapor deposition, or preferably by discrete droplet-on-demand fluid jetting technology. When spraying, dipping, electrostatic deposition, ultrasonic spraying, vapor deposition, or similar techniques are employed, a conventional masking scheme can be beneficially employed to limit deposition to the hole or to several or all of the holes in a stent. Discrete droplet-on-demand fluid-jetting is a preferred deposition method because it provides the ability to introduce precise volumes of liquid drugs or drugs-in-solution into precisely programmable locations. Discrete droplet-on-demand fluid jetting may be accomplished using commercially available fluid-jet print head jetting devices as are available (for example, not limitation) from MicroFab Technologies, Inc., of Plano, Tex. When the drug 410 is a liquid or a drug-in-solution, it is preferably dried or otherwise hardened before proceeding to the next step. The drying or hardening step may include baking, low temperature baking, or vacuum evaporation, as examples.

Figure 14C:
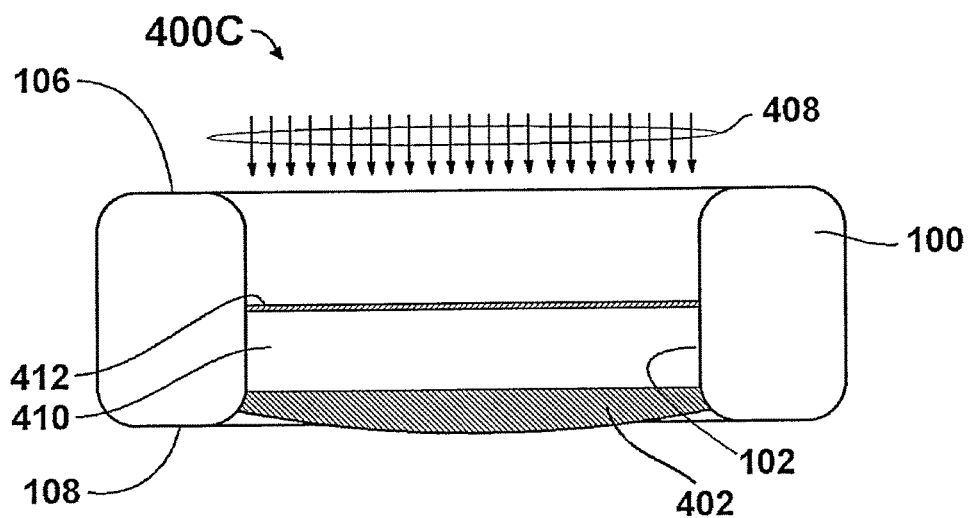

FIG. 14C shows sectional view 400C of a strut of a stent illustrating a step in the formation of a drug-loaded through-hole in a stent 100 following the step shown in FIG. 14B. In the step shown in FIG. 14C, the drug 410 deposited in the hole 102 in the stent 100 is irradiated by a beam 408, preferably a GCIB or an accelerated Neutral Beam, to form a thin barrier layer 412 by modification of a thin upper region of the drug 410. The thin barrier layer 412 consists of drug 410 modified to densify, carbonize or partially carbonize, denature, cross-link, or polymerize molecules of the drug in the thin uppermost layer of the drug 410. The thin barrier layer 412 may have a thickness on the order of about 10 nanometers or even less. In modifying the surface a beam 408 comprising preferably argon or another inert gas in the form of accelerated cluster ions, accelerated neutral clusters, or accelerated neutral monomers is employed. The beam 408 is preferably accelerated with an accelerating potential of from 5 kV to 50 kV or more. The coating layer is preferably exposed to a GCIB dose of at least about $1 \times 10^{13}$ gas cluster ions per square centimeter (or in the case of Neutral Beam, a dose that has the energy equivalent determined by thermal beam energy flux sensor). By selecting the dose and/or accelerating potential of the beam 408, the characteristics of the thin barrier layer 412 may be adjusted to permit control of the release or elution rate and/or the rate of inward diffusion of water and/or other biological fluids when the stent 100 is implanted and expanded. In general, increasing acceleration potential increases the thickness of the thin barrier layer that is formed, and modifying the GCIB or Neutral Beam dose changes the nature of the thin barrier layer by changing the degree of cross linking, densification, carbonization, denaturization, and/or polymerization that results. This provides means to control the rate at which drug will subsequently release or elute through the barrier and/or the rate at which water and/or biological fluids my diffuse into the drug from outside.

Figure 14D:
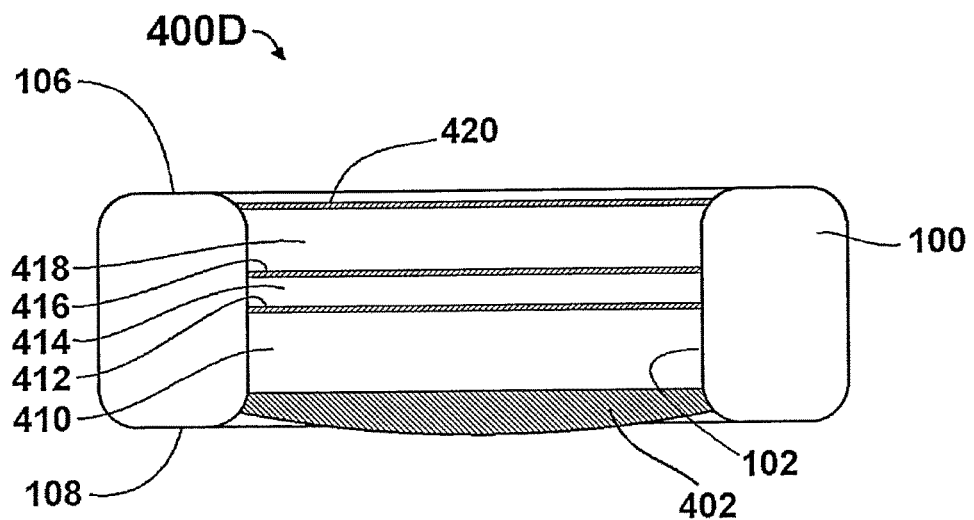

FIG. 14D shows sectional view 400D of a strut of a stent illustrating a drug-loaded through-hole in a stent 100 following the step shown in FIG. 14C. In FIG. 14D, the steps of depositing a drug and using GCIB or accelerated Neutral Beam irradiation to form a thin barrier layer in the surface of the drug has been repeated (for example) twice more beyond the stage shown in FIG. 14C. FIG. 14D shows the additional layers of drugs (414 and 418) and the additional beam-formed thin barrier layers 416 and 420. The drugs 410, 414, and 418 may be the same drug material or may be different drugs with different therapeutic modes. The thicknesses of the layers of drugs 410, 414, and 418 are shown to be different, indicating that different drug doses may be deposited in each individual layer. Alternatively, the thicknesses (and doses) may be the same in some or all layers. The properties of each of the thin barrier layers 412, 416, and 420 may also be individually adjusted by selecting GCIB or accelerated Neutral Beam properties at each barrier layer formation irradiation step by controlling the GCIB or accelerated Neutral Beam properties as discussed above. Although FIG. 14D shows a hole loaded with three layers of drugs, there is complete freedom within the constraints of the hole depth and drug deposition capabilities to utilize from one to a very large number of layers all within the spirit of the invention. The very thin barrier layers that can be formed by GCIB or accelerated Neutral Beam processing and the ability to deposit very small volumes of drug by, for example, discrete droplet-on-demand fluid-jetting technology, make many tens or even hundreds of layers possible. Each drug layer may be different or similar drug materials, may be mixtures of compatible drugs, may be larger or smaller volumes, etcetera, providing great flexibility and control in the therapeutic effect of the drug delivery system and in tailoring the sequencing and elution rates of one or more drugs.

The drug delivery system shown in FIG. 14D is an improvement over prior art systems, but it suffers from the fact that it utilizes a conventional barrier layer 402, that may consist of polymer or of other biocompatible barrier material. In the case of a stent, for example, it is generally not convenient to form a barrier layer by beam processing in the interior (lumen) surface of an unexpanded stent. Thus conventional barrier layer 402 is generally required. Use of polymers may be avoided by employing other biocompatible materials for formation of the barrier layer 402; however even so, there is risk of subsequent flaking of the material resulting in its undesired release in situ. FIGS. 5A, 5B, and 5C show another embodiment of the present invention that avoids the undesirable need to use conventional barrier materials.

Figure 15A:
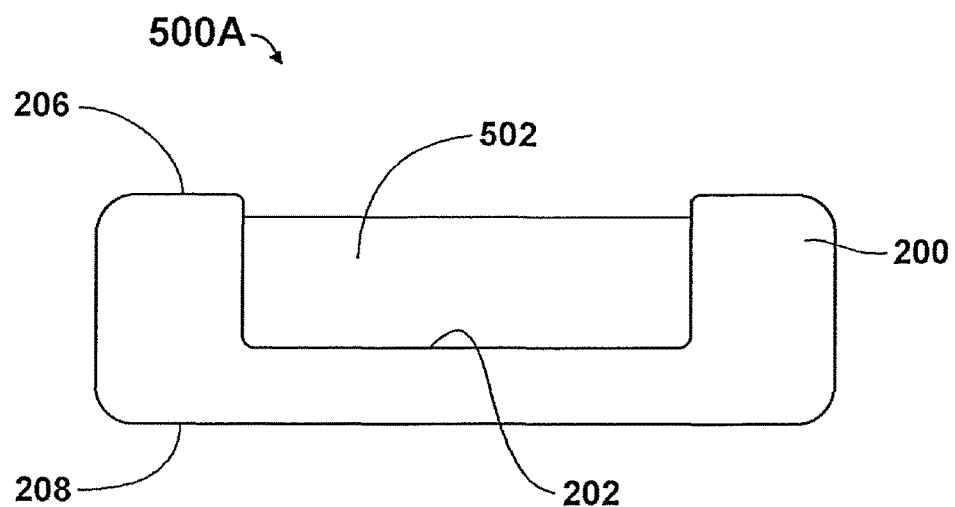
FIGS. 15A, 15B, and 15C show steps in the formation of a drug loaded blind-hole in a stent according to an embodiment of the invention.

FIG. 15A shows sectional view 500A of a strut of a stent illustrating a step in the formation of a drug-loaded blind-hole in a stent 200 according to an embodiment of the invention. A stent 200 has a blind-hole 202. The stent has an inner surface 208 forming the lumen of the stent and has an outer surface 206 forming the vascular scaffold portion of the stent. As a step in the embodiment of the invention, a drug 502 is deposited in the hole 202 in the stent 200. Not shown, and optionally, a GCIB or accelerated Neutral Beam cleaning process may be employed to clean the surfaces of the hole 202 prior to depositing drug 502 in the hole 202. The deposition of the drug 502 may be by any of the above-discussed methods. Discrete droplet-on-demand fluid jetting is a preferred deposition method because it provides the ability to introduce precise volumes of liquid drugs or drugs-in-solution into precisely programmable locations. When the drug 502 is a liquid or a drug-in-solution, it is preferably dried or otherwise hardened before proceeding to the next step. The drying or hardening may include baking, low temperature baking, or vacuum evaporation, as examples.

Figure 15B:
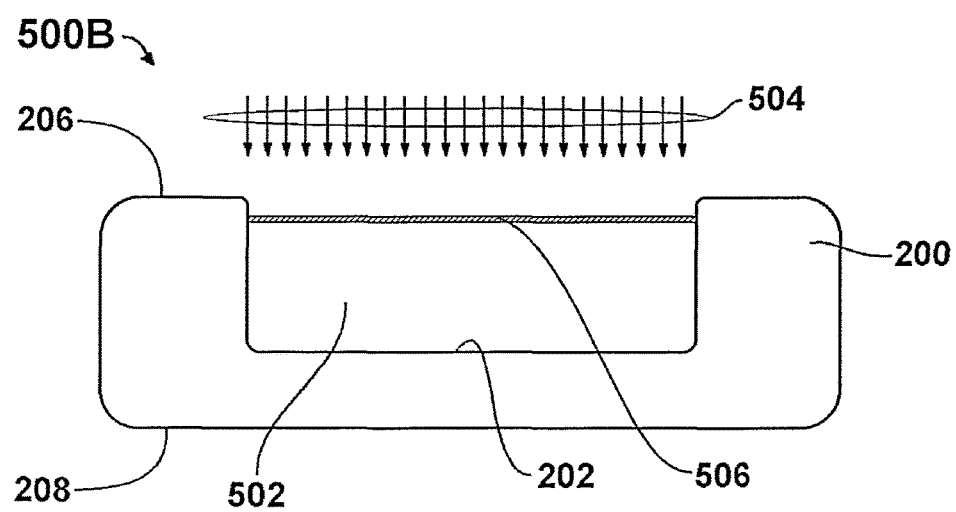

FIG. 15B shows sectional view 500B of a strut of a stent illustrating a step in the formation of a drug-loaded blind-hole in a stent 200 following the step shown in FIG. 15A. In the step shown in FIG. 15B, the drug 502 deposited in the hole 202 in the stent 200 is irradiated by a beam 504, preferably a GCIB or an accelerated Neutral Beam to form a thin barrier layer 506 by modification of a thin upper region of the drug 502. The thin barrier layer 506 consists of drug 502 modified to densify, carbonize or partially carbonize, denature, cross-link, or polymerize molecules of the drug in the thin uppermost layer of the drug 502. The thin barrier layer 506 may have a thickness on the order of about 10 nanometers or even less. In modifying the surface, a beam 504 comprising preferably argon or another inert gas in the form of accelerated cluster ions accelerated neutral clusters, or accelerated neutral monomers is employed. The beam 504 is preferably accelerated with an accelerating potential of from 5 kV to 50 kV or more. The coating layer is preferably exposed to a GCIB dose of at least about $1 \times 10^{13}$ gas cluster ions per square centimeter (or in the case of a Neutral Beam, a dose that has the energy equivalent determined by a thermal beam energy flux sensor). By selecting the dose and/or accelerating potential of the beam 504, the characteristics of the thin barrier layer 506 may be adjusted to permit control of the elution rate and/or the rate of inward diffusion of water and/or other biological fluids when the stent 200 is implanted and expanded. In general, increasing acceleration potential increases the thickness of the thin barrier layer that is formed, and modifying the GCIB or accelerated Neutral Beam dose changes the nature of the thin barrier layer by changing the degree of cross linking, densification, carbonization, denaturization, and/or polymerization that results. This provides means to control the rate at which drug will subsequently release or elute through the barrier and/or the rate at which water and/or biological fluids my diffuse into the drug from outside.

Figure 15C:
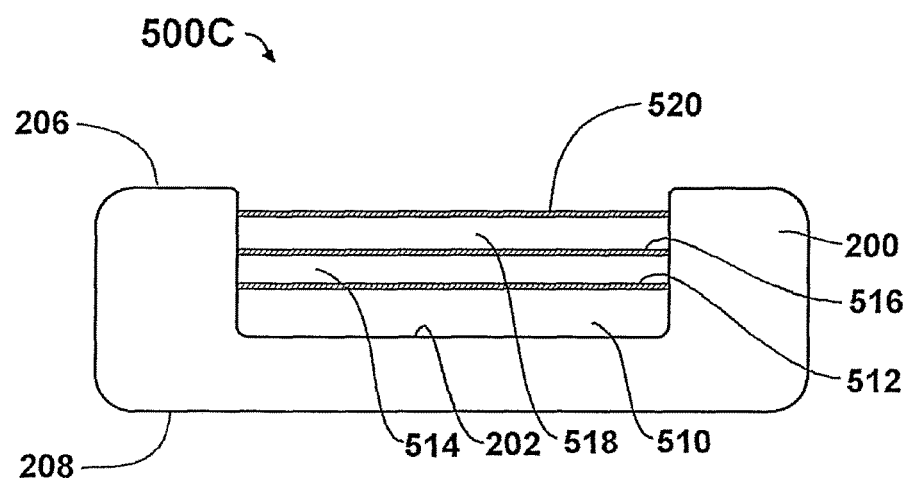

FIG. 15C shows sectional view 500C of a drug-loaded blind-hole in a stent 200 having multiple drug layers, according to an embodiment of the invention. The steps of depositing a drug and using ion beam irradiation to form a thin barrier layer in the surface of the drug has been as described above for FIGS. 5A and 5B have been applied (for example) three times in succession, forming a blind-hole 202 loaded with three drugs 510, 514, and 518, each having a thin barrier layer 512, 516, and 520 having been formed by irradiation, preferably GCIB or accelerated Neutral Beam, irradiation. The drugs 510, 514, and 518 may be the same drug material or may be different drugs with different therapeutic modes. The thicknesses of the layers of drugs 510, 514, and 518 are shown to be different, indicating that different drug doses may be deposited in each individual layer. Alternatively, the thicknesses (and doses) may be the same in some or all layers. The properties of each of the thin barrier layers 512, 516, and 520 may also be individually adjusted by controlling beam properties at each barrier layer formation irradiation step by controlling the GCIB or accelerated Neutral Beam properties as discussed above. Although three layers of drugs are shown, there is complete freedom within the constraints of the hole depth and drug deposition capabilities to utilize from one to a very large number of layers all within the spirit of the invention.

Figure 16A:
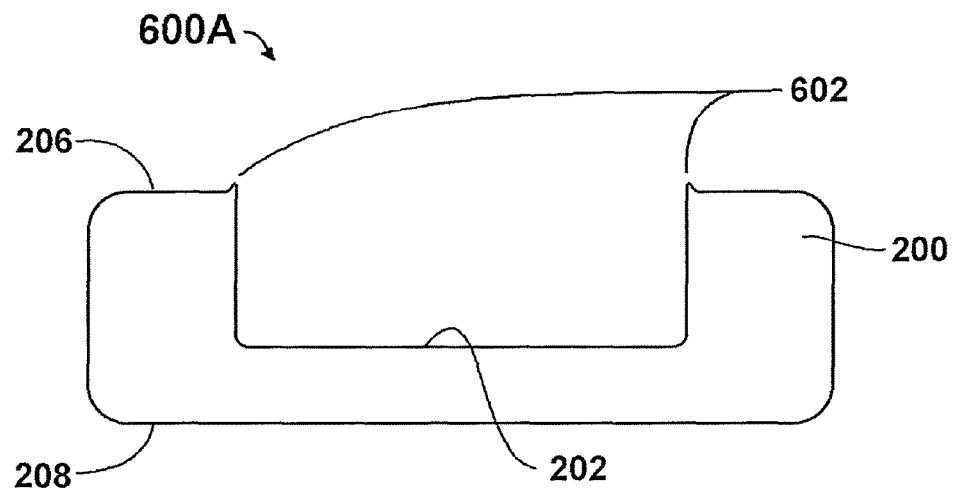
FIGS. 16A and 16B show optional steps for processing of a hole edge according to an embodiment of the invention.

FIG. 16A shows a cross section view 600A of a portion of a blind-hole in an implantable medical device (a stent 200, for example), wherein the hole 202 has been formed by laser machining and has a resulting sharp or (as shown) burred edge 602 resulting from the machining process. In most cases such an edge or burr is undesirable in an implantable medical device. GCIB or accelerated Neutral Beam processing can be advantageously employed to remove such burr or sharp edge prior to loading the hole with a drug and forming a thin barrier layer (as described above).

Figure 16B:
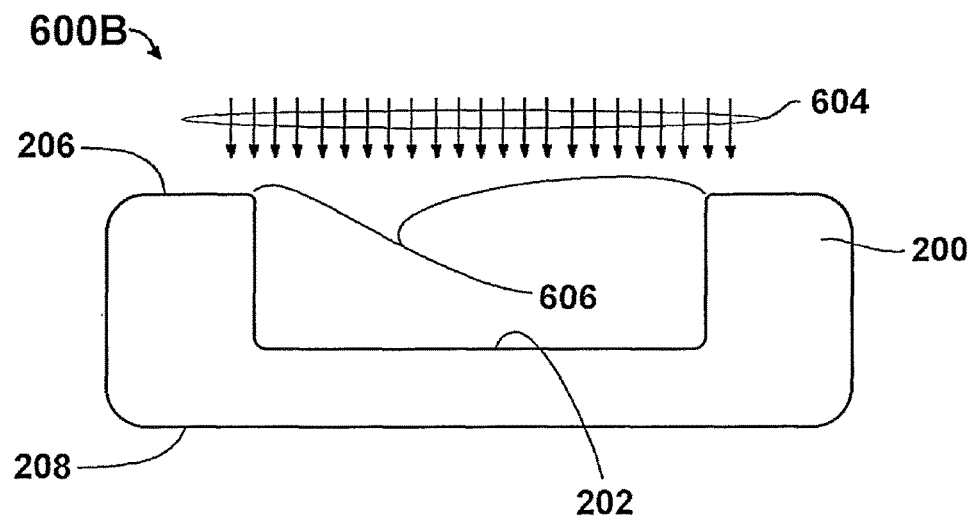

FIG. 16B shows a cross section view 600B of the hole 202 in stent 200 processed by irradiation with a beam 604, preferably a GCIB or an accelerated Neutral Beam, to remove the sharp or burred edge 602 by GCIB or accelerated Neutral Beam processing, forming a smooth edge 606. A beam 604 comprising preferably argon, another inert gas, oxygen, or nitrogen in the form of accelerated cluster ions, accelerated neutral ions, or accelerated neutral monomers is employed. The beam 604 is preferably accelerated with an accelerating potential of from 5 kV to 50 kV or more. The coating layer is preferably exposed to a GCIB dose of from about $1 \times 10^{15}$ to about $1 \times 10^{17}$ gas cluster ions per square centimeter (or in the case of Neutral Beam, a dose that has the energy equivalent determined by thermal beam energy flux sensor). By selecting the dose and/or accelerating potential of the GCIB 604, the etching characteristics of the GCIB 604 are adjusted to control the amount of etching and smoothing performed in forming smoothed edge 606. In general, increasing acceleration potential and or increasing the GCIB or accelerated Neutral Beam dose increases the etching rate.

Figure 17:
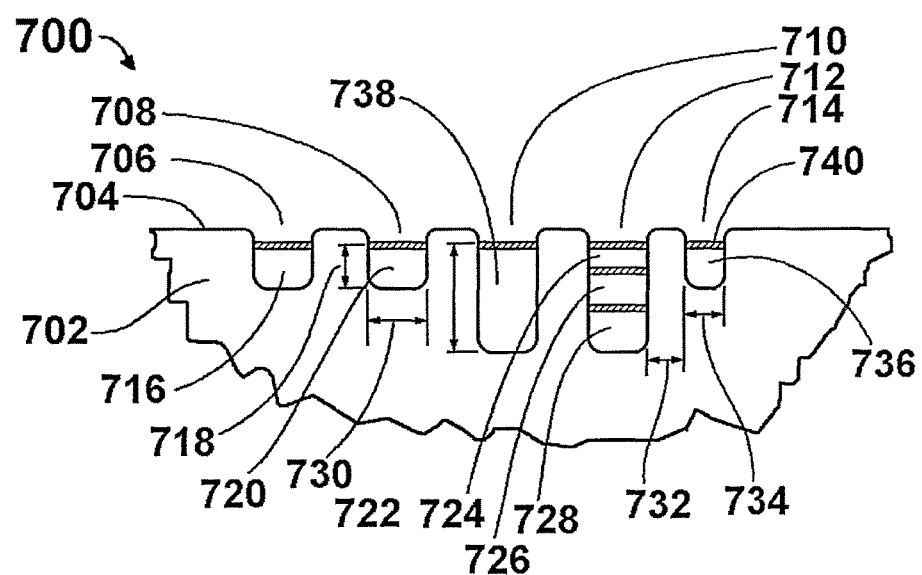
FIG. 17 shows a cross section view of a portion of a surface of an implantable medical device, illustrating the variety of methods that can be employed within the present invention to control drug administration.

FIG. 17 shows a cross sectional view 700 of the surface 704 of a portion 702 of a non-polymer implantable medical device having a variety of drug-loaded holes 706, 708, 710, 712, and 714 pointing out the diversity and flexibility of the invention. The implantable medical device could, for example, be any of a vascular stent, an artificial joint prosthesis, a cardiac pacemaker, or any other implantable non-polymer medical device and need not necessarily be a thin-walled device like a vascular or coronary stent. The holes all have thin barrier layers 740 formed according to the invention on one or more layers of drug in each hole. For simplicity, not all of the thin barrier layers in FIG. 17 are labeled with reference numerals, but hole 714 is shown containing a first drug 736 covered with a thin barrier layer 740 (only thin barrier layer 740 in hole 714 is labeled with a reference numeral, but each cross-hatched region in FIG. 17 indicates a thin barrier layer, and all will hereinafter be referred to by the exemplary reference numeral 740). Hole 706 contains a second drug 716 covered with a thin barrier layer 740. Hole 708 contains a third drug 720 covered with a thin barrier layer 740. Hole 710 contains a fourth drug 738 covered with a thin barrier layer 740. Hole 712 contains fifth, sixth, and seventh drugs 728, 726, and 724, each respectively covered with a thin barrier layer 740. Each of the respective drugs 716, 720, 724, 726, 728, 736, and 738 may be selected to be a different drug material or may be the same drug materials in various combinations of different or same. Each of the thin barrier layers 740 may have the same or different properties for controlling elution or release rate and/or for controlling the rate of inward diffusion of water or other biological fluids according to beam (preferably GCIB or accelerated Neutral Beam) processing principles discussed herein above. Holes 706 and 708 have the same widths and fill depth 718, and thus hold the same volume of drugs, but the drugs 716 and 720 may be different drugs for different therapeutic modes. The thin barrier layers 740 corresponding respectively to holes 706 and 708 may have either same or differing properties for providing same or different elution, release, or inward diffusion rates for the drugs contained in holes 706 and 708. Holes 708 and 710 have the same widths, but differing fill depths, 718 and 722 respectively, thus containing differing drug loads corresponding to differing doses. The thin barrier layers 740 corresponding respectively to holes 708 and 710 may have either same or differing properties for providing same or different elution, release, or inward diffusion rates for the drugs contained in holes 708 and 710. Holes 710 and 712 have the same widths 730, and have the same fill depths 722, thus containing the same total drug loads, but hole 710 is filled with a single layer of drug 738, while hole 712 is filled with multiple layers of drug 724, 726, and 728, which may each be the same or different volumes of drug representing the same or different doses and furthermore may each be different drug materials for different therapeutic modes. Each of the thin barrier layers 740 for holes 710 and 712 may have the same or different properties for providing same or different elution, release, or inward diffusion rates for the drugs contained in the holes. Holes 708 and 714 have the same fill depths 718, but have different widths and thus contain different volumes and doses of drugs 720 and 736. The thin barrier layers 740 corresponding respectively to holes 708 and 714 may have either same or differing properties for providing same or different elution, release, or inward diffusion rates for the drugs contained in holes 708 and 714. The overall hole pattern on the surface 704 of the implantable medical device and the spacing between holes 732 may additionally be selected to control the spatial distribution of drug dose across the surface of the implantable medical device. Thus there are many flexible options in the application of the invention for controlling the types and doses and dose spatial distributions and temporal release sequences and release rates and release rate temporal profiles of drugs delivered by the drug delivery system of the invention.

Figure 18A:
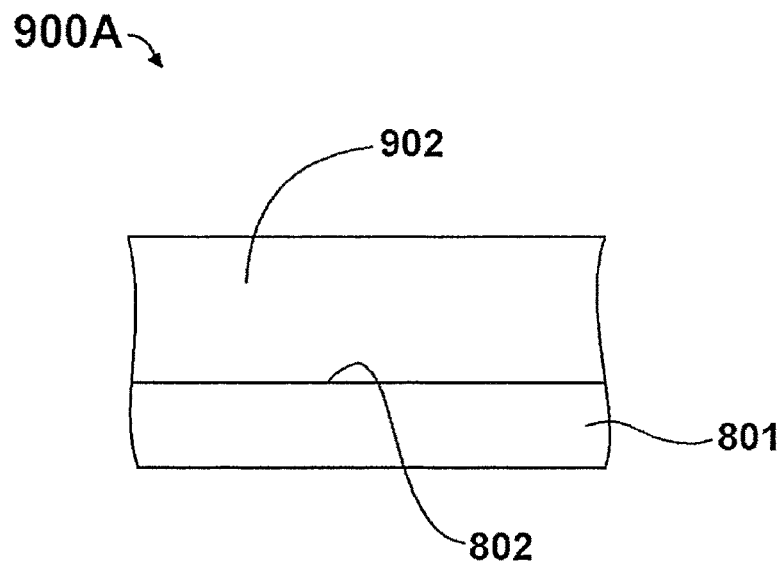
FIGS. 18A, 18B, and 18C show steps in the formation of barrier films in materials deposited on substrates, using an embodiment of the invention.

FIG. 18A shows partial sectional schematic view 900A of a substrate illustrating a step in the formation of a drug-loaded substrate 801 (which may for example be a surface on a stent or other implantable medical device) according to an embodiment of the invention. A substrate 801 has a surface 802. As a step in the embodiment of the invention, a drug 902 is deposited on the surface 802 of the substrate 801. Not shown, and optionally, a GCIB or accelerated Neutral Beam cleaning process may be employed to clean the surface 802 of the substrate 801 prior to depositing drug 902 on the surface 802. The deposition of the drug 902 may be by any of the above-discussed methods. Discrete droplet-on-demand fluid jetting is a preferred deposition method because it provides the ability to introduce precise volumes of liquid drugs or drugs-in-solution into precisely programmable locations. When the drug 902 is a liquid or a drug-in-solution, it is preferably dried or otherwise hardened before proceeding to the next step. The drying or hardening may include baking, low temperature baking, or vacuum evaporation, as examples.

Figure 18B:
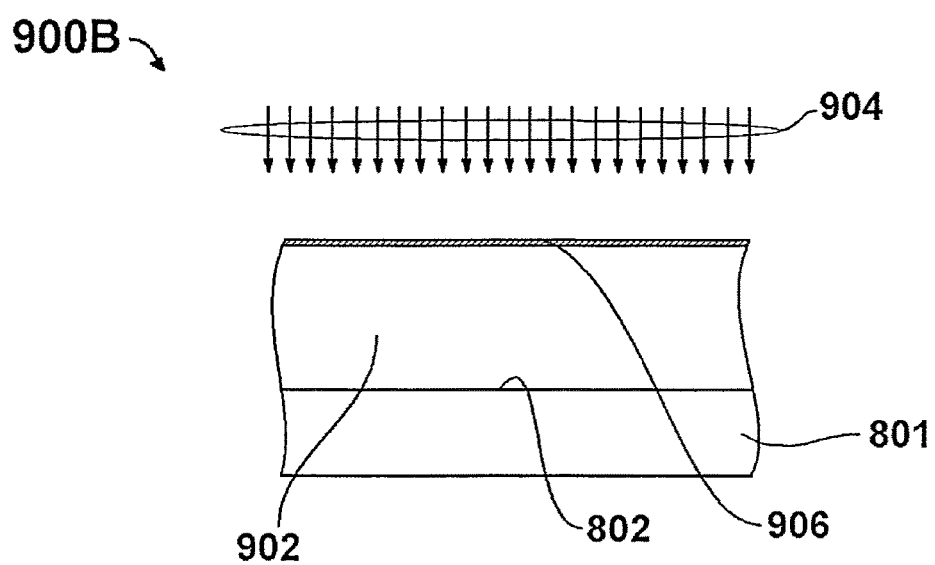

FIG. 18B shows partial sectional schematic view 900B of a substrate illustrating a step in the formation of a drug-loaded substrate 801 following the step shown in FIG. 18A. In the step shown in FIG. 18B, the drug 902 deposited on the surface 802 of the substrate 801 is irradiated by an accelerated Neutral Beam 904 to form a thin barrier layer 906 by modification of a thin upper region of the drug 902. The thin barrier layer 906 consists of drug 902 modified to densify, carbonize or partially carbonize, denature, cross-link, or polymerize molecules of the drug in the thin uppermost layer of the drug 902 by the irradiation of the accelerated Neutral Beam 904. The thin barrier layer 906 may have a thickness on the order of about 10 nanometers or even less. In modifying the surface, an accelerated Neutral Beam 904 comprising preferably argon or another inert gas in the form of accelerated neutral clusters or accelerated neutral monomers is employed. The accelerated Neutral Beam 904 is preferably accelerated with an accelerating potential of from 5 kV to 50 kV or more. The coating layer is preferably exposed to a Neutral Beam dose that has the energy equivalent (as may be determined by a thermal beam energy flux sensor) of at least about $1\times10^{13}$ gas cluster ions per square centimeter at the acceleration voltage VAcc employed. By selecting the dose and/or accelerating voltage of the accelerated Neutral Beam 904, the characteristics of the thin barrier layer 906 may be adjusted to permit control of the elution rate and/or the rate of inward diffusion of water and/or other biological fluids when the substrate 801 is implanted. In general, increasing acceleration potential increases the thickness of the thin barrier layer that is formed, and modifying the accelerated Neutral Beam dose changes the nature of the thin barrier layer by changing the degree of cross linking, densification, carbonization, denaturization, and/or polymerization that results. These parameters provide means to control the rate at which drug will subsequently release or elute through the barrier and/or the rate at which water and/or biological fluids my diffuse into the drug from outside.

Figure 18C:
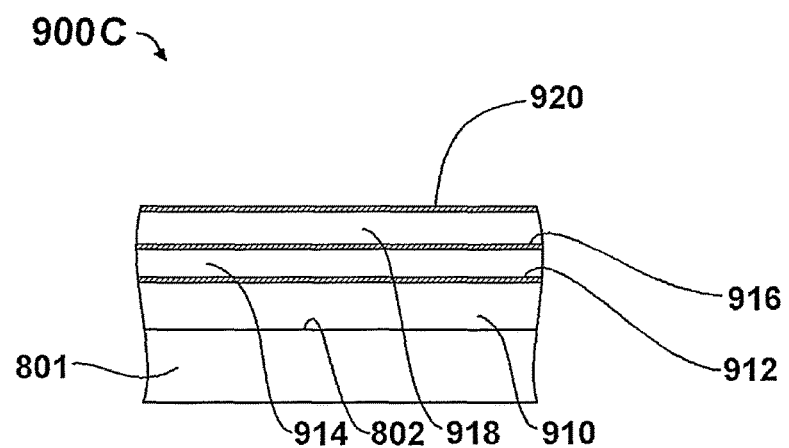

FIG. 18C shows partial sectional schematic view 900C of a drug-loaded substrate 801 having multiple drug layers and multiple barrier layers, according to an embodiment of the invention. The steps of depositing a drug and using beam irradiation to form a thin barrier layer in the surface of the drug have been as described above for FIGS. 18A and 18B have been applied (for example) three times in succession, forming a surface 802 loaded with three drugs 910, 914, and 918, each having a thin barrier layer 912, 916, and 920 having been formed by accelerated Neutral Beam irradiation. The drugs 910, 914, and 918 may be the same drug material or may be different drugs with different therapeutic modes. The thicknesses of the layers of drugs 910, 914, and 918 are shown to be different, indicating the possibility that different drug doses may be deposited in each individual layer. Alternatively, the thicknesses (and/or doses) may be the same in some or all layers. The properties of each of the thin barrier layers 912, 916, and 920 may also be individually adjusted by controlling beam properties at each barrier layer formation irradiation step by controlling the accelerated Neutral Beam properties as discussed above. Although three layers of drugs are shown, there is complete freedom within the constraints of the drug deposition capabilities to utilize from one to a very large number of layers all within the spirit of the invention.

Studies have suggested that a wide variety of drugs may be useful at the site of contact between the medical device and the in situ environment. For example, drugs such as anti-coagulants, anti-prolifics, antibiotics, immune-suppressing agents, vasodilators, anti-thrombotic substances, anti-platelet substances, and cholesterol reducing agents may reduce instances of restenosis when diffused into the blood vessel wall after insertion of the stent. Although the present invention is described in reference to stents, its applications and the claims hereof are not limited to stents and may include any contact with a living body where drug delivery may be helpful.

Although the benefits of employing the Neutral Beam for electrical charging-free processing have been described with respect to various electrically insulating and/or high electrical resistivity materials such as insulating drug coatings, polymers, and other materials, it is understood by the inventors that all materials of poor or low electrical conductivity may benefit from using the Neutral Beam of the invention as a substitute for processing using techniques that transfer charges, like ion beams (including GCIB), plasmas, etc. It is intended that the scope of the invention includes all such materials. It is further understood by the inventors that Neutral Beam processing is often advantageous as compared to GCIB and other ion beams, beyond the advantage of reduced surface charging. Thus it is also valuable for processing even materials that are electrically conductive (such as, for example, metal stents or other metal medical devices or components), due to other the advantages of Neutral Beam processing, especially of neutral monomer beam processing, which produces less surface damage, better smoothing, and smoother interfaces between processed and underlying unprocessed regions, even in metals and highly conductive materials. It is intended that the scope of the invention include processing of such materials.

Although the benefits of employing Neutral Beam for modifying the surfaces of drug materials on medical devices to control an elution rate of a drug in a fluid environment have been disclosed as an example, it is understood by the inventors that surfaces of other organic or even some inorganic materials on other types of substrates may be modified to change the rate at which they elute or release material in a fluid environment, or evaporate or sublimate or release material in an air or other gaseous environment or in a vacuum. It is intended that the scope of the invention include processing of such materials using accelerated Neutral Beams derived from accelerated GCIBs. Such materials may be in the form of a coating on a substrate or in a bulk material form.

Although the invention has been described with respect to various embodiments, it should be realized this invention is also capable of a wide variety of further and other embodiments within the spirit and scope of the invention and the appended claims.

What is claimed is:

1. A method of modifying a surface of a medical device comprising the steps:
   a. depositing a first drug coating layer on at least a portion of the surface of the medical device;
   b. depositing one or more additional drug coating layers on the first drug coating layer to form a plurality of drug coating layers;
   c. forming an accelerated and focused Neutral Beam comprising the steps of forming a gas cluster ion beam, accelerating and focusing the gas cluster ion beam to form an accelerated gas cluster beam, promoting dissociation of gas clusters in the accelerated gas cluster ion beam, and removing ions from the accelerated gas cluster ion beam to form an accelerated and focused Neutral Beam; and
   d. irradiating a first exposed surface of at least one of the first drug coating layer or the one or more additional drug coating layers with the accelerated and focused Neutral Beam to form a first barrier layer from the first drug coating layer or the one or more additional deposited drug coating layers of the first exposed surface and at the first exposed surface.

2. The method of claim 1, further comprising the steps, prior to the depositing step a.: forming a second beam; and second irradiating at least a portion of the surface of the medical device with the second beam to: clean the at least a portion of the surface of the medical device; smooth the at least a portion of the surface of the medical device; or remove a sharp or burred edge on the at least a portion of the surface of the medical device.

3. The method of claim 1, wherein the irradiating step d. forms the barrier layer by modifying the drug of the first drug coating layer or of the one or more additional drug coating layers at the exposed surface by: cross-linking molecules of the drug; densifying the drug; carbonizing the drug; polymerizing the drug; or denaturing the drug.

4. The method of claim 1, wherein the first barrier layer controls a rate of inward diffusion of a fluid into the first drug coating layer or the one or more drug containing layers.

5. The method of claim 1, wherein the first barrier layer controls a rate of outward elution of drug from the drug coating.

6. The method of claim 1, comprising the additional steps forming a third beam and irradiating a second exposed surface of at least one of the first drug coating layer or the one or more additional drug coating layers with the third beam to form a second barrier layer at the second exposed surface.

7. The method of claim 6, wherein the third beam is a Neutral Beam.

8. The method of claim 6, wherein the third beam is a gas cluster ion beam.

9. The method of claim 6, wherein the first barrier layer and the second barrier layer have different properties for differently controlling elution rates of two drug coating layers.

10. The method of claim 1, where the first drug coating layer and an additional drug coating layer comprise different drug materials.

11. A method of modifying a surface of a medical device comprising the steps:
   a. depositing a drug coating layer on at least a portion of the surface of the medical device to form a deposited drug coating layer
   b. forming an accelerated and focused Neutral Beam comprising the steps of forming a gas cluster ion beam, accelerating and focusing the gas cluster ion beam to form an accelerated gas cluster ion beam, promoting dissociation of gas clusters in the accelerated gas cluster ion beam, and removing ions from the accelerated gas cluster ion beam to form an accelerated and focused Neutral Beam; and
   c. irradiating an exposed surface of the drug coating layer with the accelerated and focused Neutral Beam to form a barrier layer from the deposited drug coating layer and at the exposed surface.

12. The method of claim 11, further comprising depositing one or more additional drug coating layers on the at least a portion of the surface of the medical device to form a plurality of drug coating layers, prior to the step of irradiating.

* * * * *